(12) United States Patent
Aguiar et al.

(10) Patent No.: US 11,602,454 B1
(45) Date of Patent: Mar. 14, 2023

(54) TEMPERATURE MODULATION ASSEMBLY AND A MULTI-LAYER RETENTION MECHANISM FOR A TEMPERATURE THERAPY DEVICE

(71) Applicant: Hyper Ice, Inc., Irvine, CA (US)

(72) Inventors: Alexander Joseph Aguiar, San Diego, CA (US); Daniel Royal Evans, San Diego, CA (US); Robert Glen Edwards, San Diego, CA (US); Trevor Austin Kerth, San Diego, CA (US)

(73) Assignee: Hyper Ice, Inc., Irvine, CA (US)

( * ) Notice: Subject to any disclaimer, the term of this patent is extended or adjusted under 35 U.S.C. 154(b) by 44 days.

(21) Appl. No.: 17/308,012

(22) Filed: May 4, 2021

Related U.S. Application Data

(60) Provisional application No. 63/090,987, filed on Oct. 13, 2020.

(51) Int. Cl.
*A61F 7/00* (2006.01)

(52) U.S. Cl.
CPC ...... *A61F 7/007* (2013.01); *A61F 2007/0024* (2013.01); *A61F 2007/0032* (2013.01); *A61F 2007/0042* (2013.01); *A61F 2007/0075* (2013.01); *A61F 2007/0093* (2013.01)

(58) Field of Classification Search
CPC combination set(s) only.
See application file for complete search history.

(56) References Cited

U.S. PATENT DOCUMENTS

| | | |
|---|---|---|
| 4,962,761 A | 10/1990 | Golden |
| 5,080,089 A | 1/1992 | Mason et al. |
| 5,800,490 A | 9/1998 | Patz et al. |
| 5,847,929 A * | 12/1998 | Bernier ................. H01L 23/433 361/719 |
| 5,865,841 A | 2/1999 | Kolen et al. |
| 5,871,526 A | 2/1999 | Gibbs et al. |

(Continued)

FOREIGN PATENT DOCUMENTS

CA  2356993 A1  7/2000

OTHER PUBLICATIONS

U.S. Appl. No. 15/818,308 U.S. Pat. No. 10,406,024, Wearable Temperature Therapy System and Method, filed Nov. 20, 2017.

(Continued)

*Primary Examiner* — Joseph A Stoklosa
*Assistant Examiner* — Adam J Avigan
(74) *Attorney, Agent, or Firm* — Goodwin Procter LLP

(57) ABSTRACT

A temperature modulation assembly and a multi-layer retention mechanism for such a temperature therapy device are disclosed. According to one embodiment, a temperature modulation assembly for a temperature therapy device has a heat spreader and a mounting plate coupled to a bottom portion of a spacer, wherein the heat spreader is disposed between the mounting plate and the spacer. The temperature modulation assembly has a heatsink and a fan coupled to a top portion of the spacer, wherein the heatsink is disposed between the top portion of the spacer and the fan. The temperature modulation assembly further includes a heating and/or cooling device disposed within a central opening of the spacer, wherein the heating and/or cooling device is located between the heatsink and the heat spreader.

16 Claims, 18 Drawing Sheets

(56) References Cited

U.S. PATENT DOCUMENTS

| | | |
|---|---|---|
| 6,818,012 B2 | 11/2004 | Ellingboe |
| 8,425,579 B1 | 4/2013 | Edelman et al. |
| 10,406,024 B2 | 9/2019 | Evans et al. |
| 2003/0097845 A1 | 5/2003 | Saunders et al. |
| 2005/0075593 A1 | 4/2005 | Smith et al. |
| 2005/0193742 A1 | 9/2005 | Arnold |
| 2008/0046047 A1 | 2/2008 | Jacobs |
| 2008/0188915 A1* | 8/2008 | Mills .................. A61F 7/007 607/112 |
| 2010/0198322 A1 | 8/2010 | Joseph et al. |
| 2012/0179231 A1 | 7/2012 | Dewaegenaere |
| 2013/0085552 A1 | 4/2013 | Mandel |
| 2013/0087180 A1 | 4/2013 | Stark et al. |
| 2014/0102204 A1* | 4/2014 | Akiyama ............ A61B 5/0095 73/655 |
| 2014/0260330 A1* | 9/2014 | Karlstedt ............... F25B 21/02 62/3.3 |
| 2014/0352325 A1 | 12/2014 | Brown |
| 2015/0101788 A1 | 4/2015 | Smith et al. |
| 2017/0325975 A1* | 11/2017 | LeRoy .................. A61F 2/7812 |
| 2018/0098903 A1 | 4/2018 | Vergara et al. |
| 2018/0110266 A1 | 4/2018 | Lee et al. |
| 2018/0147086 A1* | 5/2018 | Evans ...................... A61F 7/02 |
| 2019/0099286 A1* | 4/2019 | Myers .................. A61F 2/7812 |

OTHER PUBLICATIONS

U.S. Appl. No. 16/525,407, Wearable Temperature Therapy System and Method, filed Jul. 29, 2019.

U.S. Appl. No. 17/307,981, A Temperature Modulation Assembly and a Multilayer Retention Mechanism for a Temperature Therapy Device, filed May 4, 2021.

Jordan, D. et al., "Electric Hot/Cold Wrap", Mechanical Engineering Capstone Projects, Northeastern Univ., (Dec. 2010), retrieved from the internet, URL:http://www.mie.neu.edu/mie/capstone/mechanical-engineering-capstone-projects, 12 pages.

\* cited by examiner

TEMPERATURE MODULATION ASSEMBLY AND A MULTI-LAYER RETENTION MECHANISM FOR A TEMPERATURE THERAPY DEVICE

CROSS-REFERENCE TO RELATED APPLICATIONS

This application claims priority and benefit from U.S. Provisional Application No. 63/090,987, titled "Flexible Heat Spreader System and Method" and filed on Oct. 13, 2020, which is hereby incorporated by reference herein in its entirety.

TECHNICAL FIELD

The present disclosure relates generally to the physical therapy and/or temperature therapy field, and more specifically a temperature modulation assembly and a multi-layer retention mechanism for a temperature therapy device.

BACKGROUND

Temperature therapy or "thermal therapy" (e.g., hot and cold therapy) has been shown to be effective in injury recovery, helping to expedite the healing process while reducing pain, inflammation, and joint stiffness. Localized cooling can induce vasoconstriction with reflexive vasodilation and/or reduce bleeding, inflammation, metabolism, muscle spasm, pain, enzymatic activity, oxygen demand, and/or swelling in areas of the body affected by soft tissue trauma or injury. Localized heating can increase blood flow, decrease sensation of pain, increase local tissue metabolic rate, increase the rate of healing, and/or facilitate the stretching of tissue.

Conventional temperature therapy devices such as electric heating pads, and ice packs have a limited duration of usefulness, e.g., re-usability, before they become ineffective and/or must be decommissioned. Also, such conventional temperature therapy devices can typically require pre-cooling or pre-heating, e.g., using a refrigerator, a microwave, among other external cooling/heating devices. Additionally, in using such conventional temperature therapy devices, an injured user can often be inconvenienced by having to be close to or make use of an external cooling/heating element to make effective use of the temperature therapy device. Therefore, typical temperature therapy devices may disrupt the required rest/recovery of a user, and can contribute to hindering of recovery times. Due to these and other the limitations of current temperature therapy devices, it can further be difficult for temperature therapy devices to be made in smaller form factors and to be easily transported.

The foregoing examples of the related art and limitations therewith are intended to be illustrative and not exclusive, and are not admitted to be "prior art." Other limitations of the related art will become apparent to those of skill in the art upon a reading of the specification and a study of the drawings.

SUMMARY

A temperature modulation assembly and a multi-layer retention mechanism for such a temperature therapy device are disclosed. According to one embodiment, a temperature modulation assembly for a temperature therapy device has a heat spreader and a mounting plate coupled to a bottom portion of a spacer, wherein the heat spreader is disposed between the mounting plate and the spacer. The temperature modulation assembly has a heatsink and a fan coupled to a top portion of the spacer, wherein the heatsink is disposed between the top portion of the spacer and the fan. The temperature modulation assembly further includes a heating and/or cooling device disposed within a central opening of the spacer, wherein the heating and/or cooling device is located between the heatsink and the heat spreader.

The above and other preferred features, including various novel details of implementation and combination of events, will now be more particularly described with reference to the accompanying figures and pointed out in the claims. It will be understood that the particular systems and methods described herein are shown by way of illustration only and not as limitations. As will be understood by those skilled in the art, the principles and features described herein may be employed in various and numerous embodiments without departing from the scope of any of the present inventions. As can be appreciated from foregoing and following description, each and every feature described herein, and each and every combination of two or more such features, is included within the scope of the present disclosure provided that the features included in such a combination are not mutually inconsistent. In addition, any feature or combination of features may be specifically excluded from any embodiment of any of the present inventions.

BRIEF DESCRIPTION OF THE DRAWINGS

The accompanying figures, which are included as part of the present specification, illustrate the presently preferred embodiments and together with the general description given above and the detailed description of the preferred embodiments given below serve to explain and teach the principles described herein.

Figure 1A:
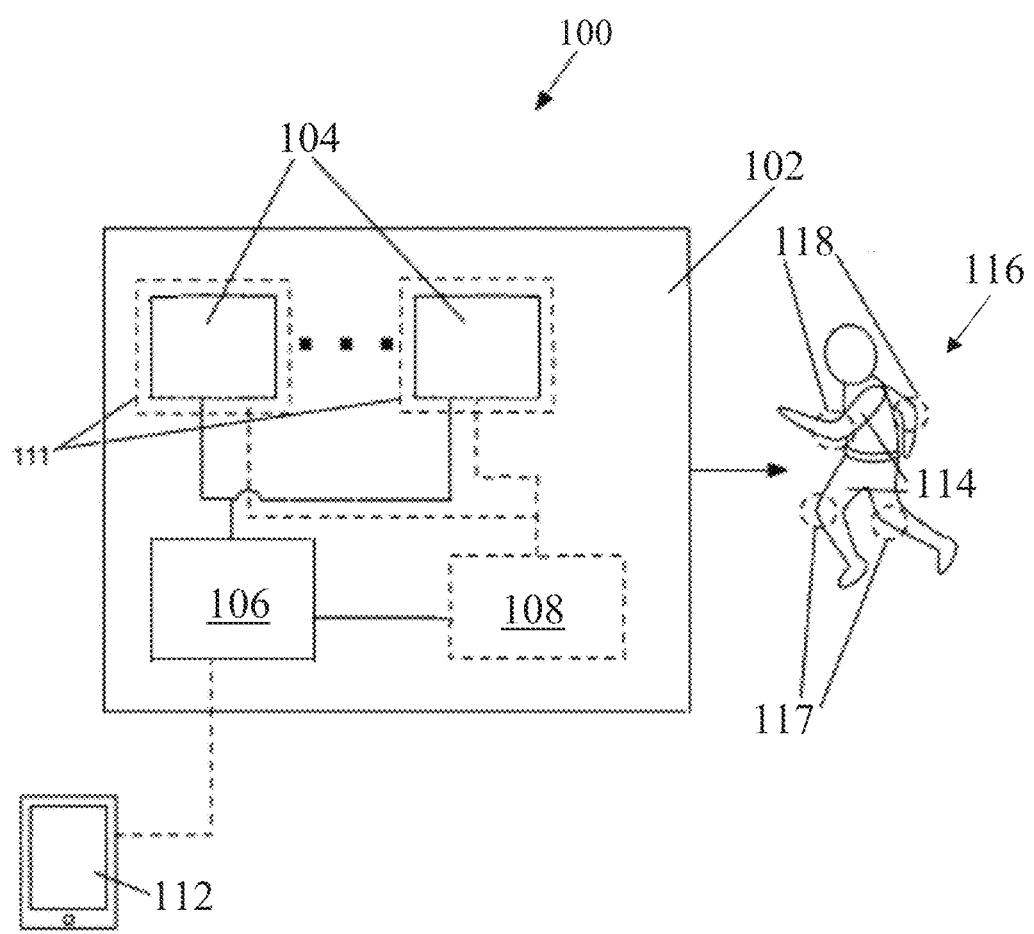
FIG. 1A illustrates a block diagram of a temperature therapy device, according to some embodiments.

While the present disclosure is subject to various modifications and alternative forms, specific embodiments thereof have been shown by way of example in the drawings and will herein be described in detail. The present disclosure should be understood to not be limited to the particular forms disclosed, but on the contrary, the intention is to cover all modifications, equivalents, and alternatives falling within the spirit and scope of the present disclosure.

DETAILED DESCRIPTION

A temperature therapy device including a temperature modulation assembly (e.g., temperature modulation system) and a multi-layer retention mechanism are disclosed.

The temperature modulation assembly can be configured to couple and secure a plurality of components for a temperature therapy device. The temperature modulation assembly can include a mounting plate, a heat spreader, a thermoelectric cooler (TEC), a spacer, a heatsink, a fan, a cover, and a cap which can be packaged together in a compact arrangement. In some embodiments, the mounting plate can be mounted to the spacer, and the heat spreader can be secured between the mounting plate and the spacer. In an example, the mounting plate can be an aluminum mounting plate. In some embodiments, the heat spreader can include 3 layers: a top layer including a first adhesive (e.g., a first silicone adhesive layer) layer, a middle layer 342 including graphite/graphene and a bottom layer also including a second adhesive layer (e.g., a second silicone adhesive layer). In some embodiments, a primer can be disposed on the bottom layer of the heat spreader, where the primer can be configured to bond a silicone adhesive on the mounting plate and/or on a silicone overmold insert to the bottom layer (e.g., also a silicone adhesive layer) of the heat spreader. In some embodiments, the heatsink can be fitted and/or secured to the temperature therapy device by mounting the fan to the spacer, where the heatsink can be secured between the fan and the spacer. In some embodiments, a cover can be placed over the spacer, heatsink and fan, where the cover can include vents (e.g., vents configured to allow airflow to and/or from the heatsink). In some embodiments, the cover can also secure a portion of a flexible fabric (e.g., a top layer of a multi-layer retention mechanism) to the spacer. In some embodiments, a cap can be placed onto the cover, where the cap can include openings that are configured to allow for additional structural support and air intake into the temperature modulation assembly.

The multi-layer retention mechanism can be configured to retain components (e.g., flexible components) of the temperature therapy device. The multi-layer retention mechanism can include a top layer including control module, and a bottom layer including a silicone overmold insert. In some embodiments, the top layer can also include a flexible fabric and/or an elastic material. In an example, the top layer can include spandex. In some embodiments, the control module can include an electronics housing and electronic parts inside the electronics housing. In some embodiments, the bottom layer can include one or more boning mechanisms, one or more structural support pieces, one or more straps and one or more locking mechanisms. In some embodiments, the bottom layer can include polyester and/or spandex. In some embodiments, the bottom layer can include polyester only. In some embodiments, the straps can be coupled indirectly to the boning mechanism. In an example, the straps can be sewn into bottom layer adjacent the boning mechanism to mechanically couple the straps, bottom layer and boning mechanisms together. In some embodiments, the boning mechanisms can include a flat spring that is flexible in one direction but inflexible in another, e.g., perpendicular, direction. In some embodiments, the boning mechanism can include metal and/or a metal spring. In some examples, the boning mechanism can include a steel spring.

Referring to FIG. 1A, a block diagram of a temperature therapy device 100 is presented, according to some embodiments. In some embodiments, the temperature therapy device 100 can include a multi-layer retention mechanism 102, a temperature modulation assembly 104 retained 111 by the multi-layer retention mechanism 102 (e.g., one or more straps, buckles, fabric layers, etc.), and a control module 106 communicatively coupled to the temperature modulation assembly 104 and also retained by the multi-layer retention mechanism 102. In some embodiments, the multi-layer retention mechanism 102 can include one or more (e.g., all) flexible and/or elastic components of the temperature therapy device 100. In an example, the multi-layer retention mechanism can include a flexible substrate. In some embodiments, the temperature modulation assembly 104 can include a fan, a heatsink and a thermoelectric cooler (TEC). In some embodiments, the temperature modulation assembly 104 can be configured to couple and secure a plurality of components of a temperature therapy device 100 in a compact arrangement. In some embodiments, the temperature modulation assembly 104 can include, e.g., be coupled to, a portion of the multi-layer retention mechanism 102. In some embodiments, the temperature therapy device 100 can include one or more temperature modulation assemblies 104, as shown. In some embodiments, the temperature therapy device 100 can also include a power supply module 108 retained by the multi-layer retention mechanism 102. The power supply module 108 can be electrically coupled to the temperature modulation assembly 104 and the control module 106. In some embodiments, the power supply module 108 may not be retained by the multi-layer retention mechanism 102. In an example, the power supply module 108 can instead be built into the control module 106. In one example, the power supply module 108 can be optional, where the control module 106 can include and/or perform all the functions of the power supply module 108. The temperature therapy device 100 can also include a client application executing at a mobile device 112 in communication with the control module 106, and any other suitable components. In some embodiments, the temperature therapy device 100 can include and/or can also be referred to as a wearable cooling and heating system.

Functions of a Temperature Therapy Device

Referring again to FIG. 1A, the temperature therapy device 100 can function to provide temperature regulated cold and/or hot therapy to a body region 114 of the user 116. In specific examples, the temperature therapy device 100 can provide both cold and hot therapy the user 116, with rapid transitions between hot and cold therapy provision modes (e.g., heating mode, cooling mode, etc.) of operation. In an example, the temperature therapy device 100 can use the multi-layer retention mechanism 102 and the temperature modulation assembly 104 to provide the temperature therapy to a body region 114 of a user 116. The temperature therapy device 100 can also function to regulate the temperature of the hot or cold therapy based on received control instructions (e.g., from a mobile application-based controller, a computing device, a mobile computing platform 112, a client application execution thereon, etc.). The temperature therapy device 100 can also function to monitor and/or track parameters of therapy provision, for example, the temperature of the hot or cold therapy being provided, the power and/or energy usage of the system during therapy provision, and/or any other suitable parameters. The temperature therapy device 100 can also function to track user data such as frequency of use (e.g., daily, hourly, monthly, etc.), duration of use (e.g., total duration in minutes, duration on a per-operating-mode basis, duration on a per-contiguous-use basis, etc.) and therapy selection (e.g., heat therapy, cold therapy), and provide tracked user data to an entity (e.g., the user, a physical therapist associated with the user, etc.), in order to guide automated modes of therapy provision to the user.

The temperature therapy device 100 may be worn by the user 116. Referring again to FIG. 1A, the temperature therapy device 100 can be positioned at a musculoskeletal region of the user 117, 118 (e.g., a knee region 117, a lower back region, an elbow region 118, etc.). However, the temperature therapy device 100 can additionally or alternatively include multiple instances of the temperature therapy device but in the same or different configurations, that can be positioned at disparate regions of the user (e.g., knee region 117, a lower back region, elbow region 118, any other suitable musculoskeletal region, etc.). The system can preferably be placed around a knee region 117 of a user, arranging one or more temperature modulation subsystems proximal to a knee cap region of a user. Additionally or alternatively, the temperature therapy device 100 can be placed around a torso region of a user, positioning the temperature modulation subsystem(s) proximal to another musculoskeletal region (e.g., a lower back region).

Figure 1B:
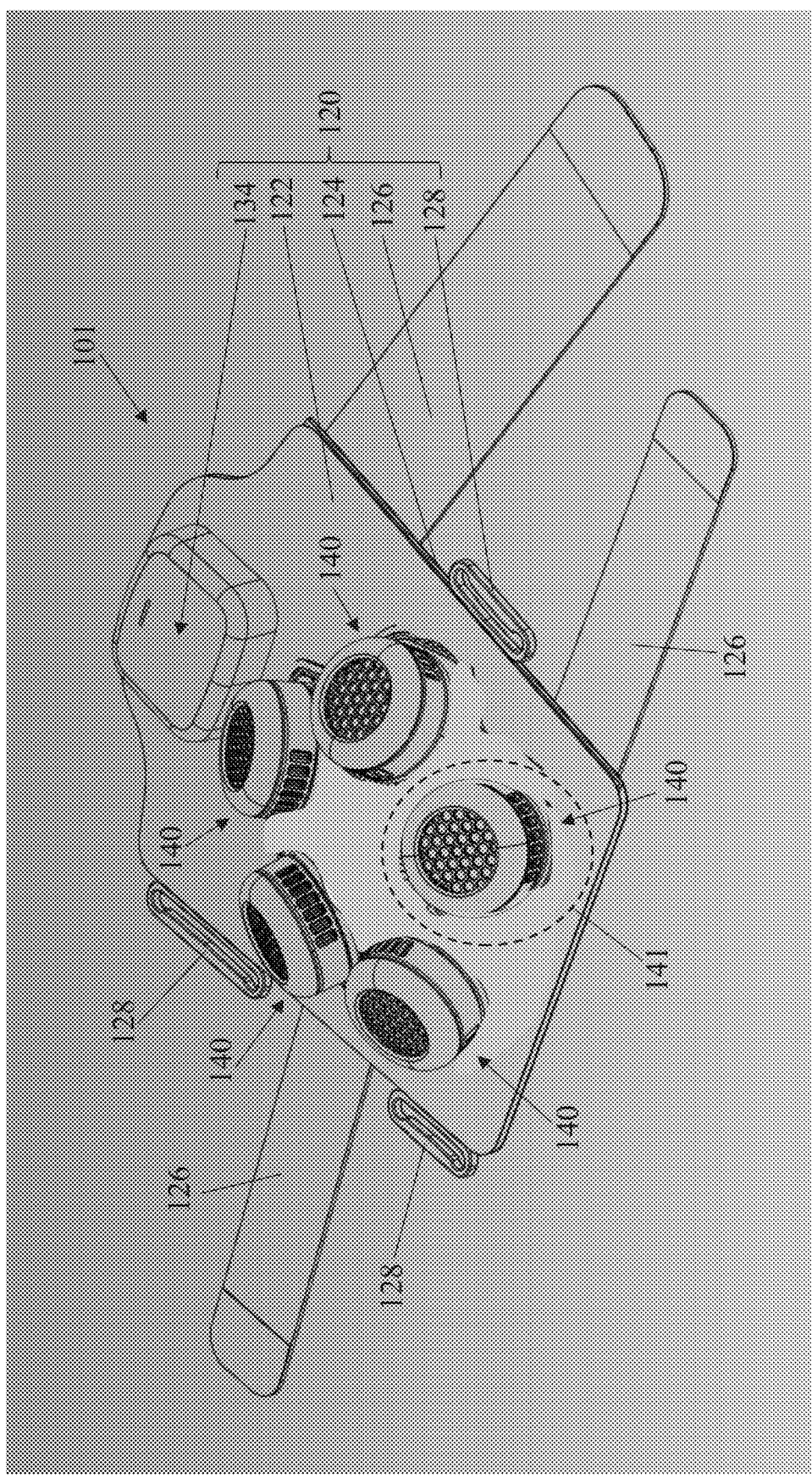
FIG. 1B illustrates an exemplary temperature therapy device, according to some embodiments.

Referring to FIG. 1B, an exemplary temperature therapy device 101 is presented, according to some embodiments. Temperature therapy device 101 of FIG. 1B can include a multi-layer retention mechanism 120 and one or more temperature modulation assemblies 140, among other components.

The multi-layer retention mechanism 120 can include flexible and/or elastic components of the temperature therapy device 101. The multi-layer retention mechanism 120 can also retain one or more temperature modulation assemblies 140 and/or the control module 134 together with at least one flexible layer of the multi-layer retention mechanism 120. In some embodiments, the multi-layer retention mechanism 120 can include a top layer 122 and a bottom layer 124. In some embodiments, the top and/or bottom layers can also be referred to as flexible layers, fabric layers, among other terms. In some embodiments, one or more straps 126 and/or locking mechanisms 128 can be coupled to the bottom layer 124. In one example, the straps 126 can be configured to wrap around the anatomy of a user and to be inserted through, and secured by, the locking mechanisms 128. In some examples, each strap 126 wraps around the anatomy of the user, is inserted through, and is secured by, the locking mechanisms to secure the temperature therapy device to the user (e.g., via buckles, hook-and-loop fasteners, any other suitable male and/or female fasteners or couplers, etc.). In some embodiments, one or more temperature modulation assemblies 140 and/or the control module 134 can be coupled to the top layer 122, as shown. As used herein, the control module 134 can also be referred to as an electronics box, collected electronics, electronics housing, among other terms.

Figure 1C:
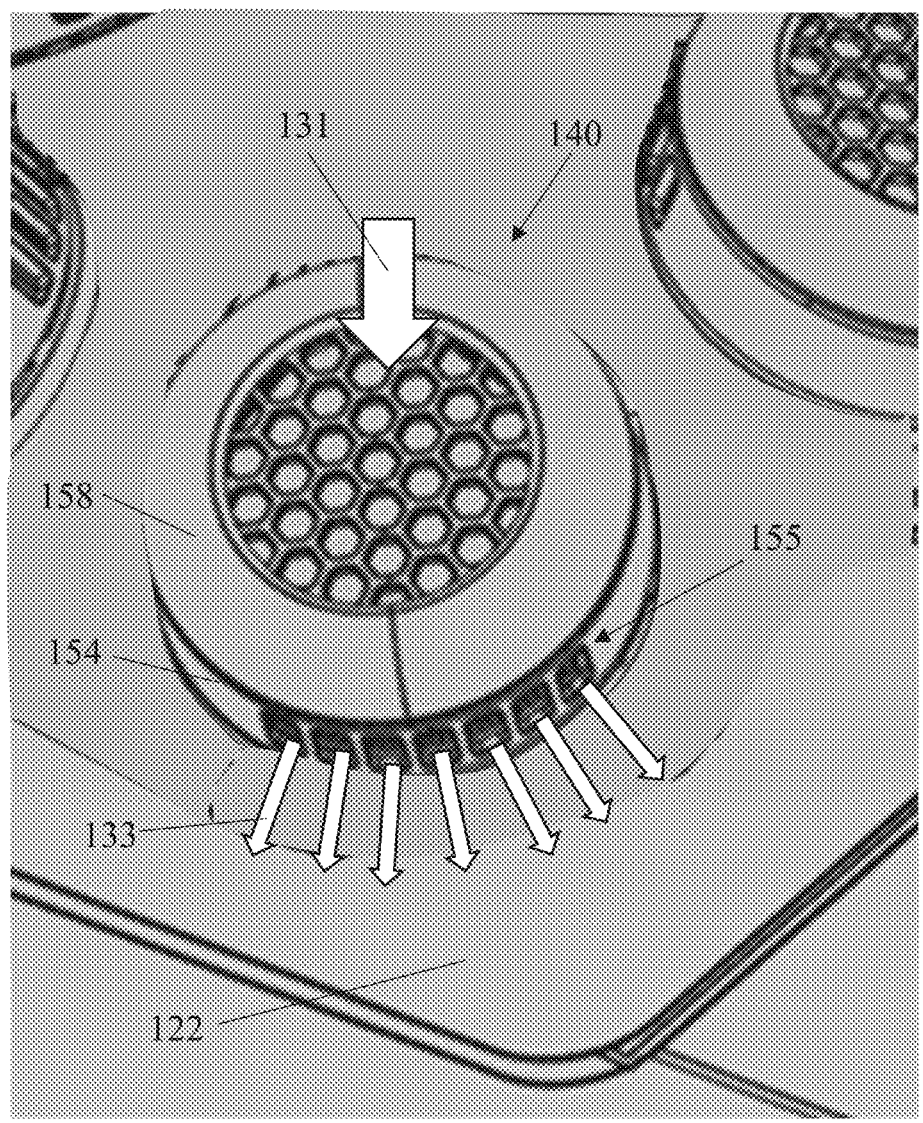
FIG. 1C illustrates a view of an exemplary temperature modulation assembly, according to some embodiments.

Referring still to FIG. 1B, in some embodiments, the temperature modulation assembly 140 can include a fan, a heatsink and a thermoelectric cooler (TEC), among other components described in detail below. In some embodiments the temperature therapy device 101 can include one or more temperature modulation assemblies 140 (e.g., as shown). Although a plurality of temperature modulation assemblies 140 are shown, in some embodiments, any suitable number of temperature modulation assemblies 140 can be used. In an example, as shown, the temperature therapy device 101 can include five of the temperature modulation assemblies 140. In some examples, one, e.g., single, temperature modulation assembly 140 is used. Thus, a temperature therapy device 101 can include one or more of the temperature modulation assemblies 140. An exemplary temperature modulation assembly 140 is encircled 141. FIG. 1C shows a zoom-in view of the encircled 141 temperature modulation assembly 140 and is further described below.

Temperature Modulation Assembly for a
Temperature Therapy Device

To effectively position and the temperature therapy components of a temperature therapy device relative to a user, and provide temperature regulated therapy to a body region of a user, it can be beneficial to package together some inelastic and elastic components of the temperature therapy device in a compact and/or portable arrangement.

Figure 1D:
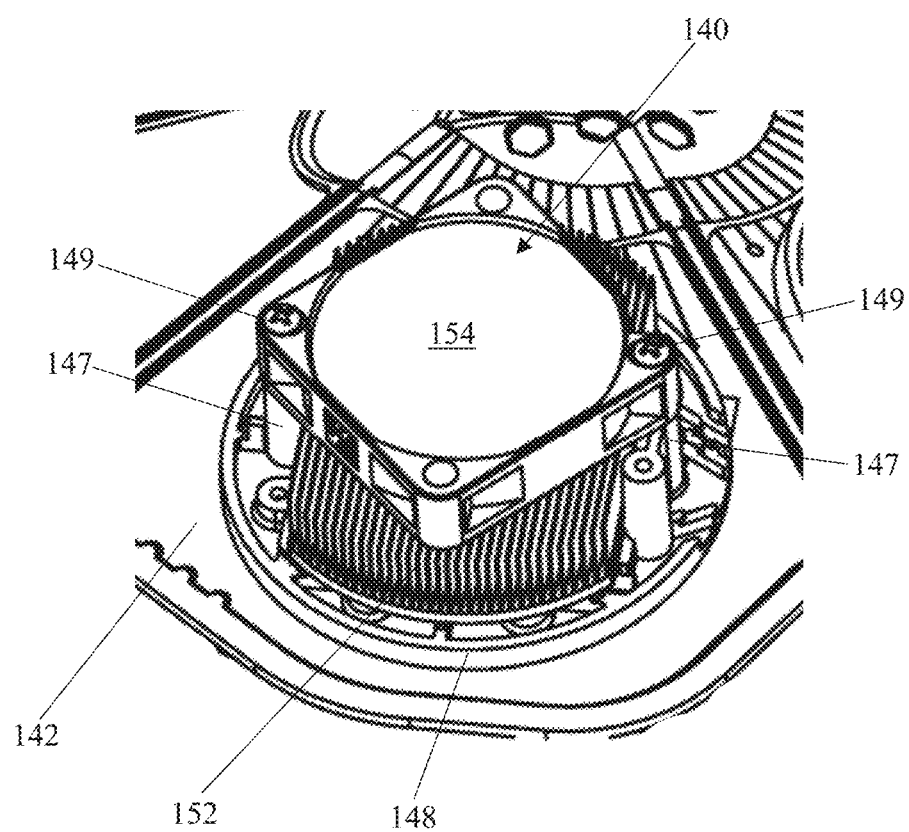
FIG. 1D illustrates a temperature modulation assembly without its cover and cap, according to some embodiments.

Referring to FIGS. 1C and 1D, multiple views of a temperature modulation assembly of a temperature therapy device are presented. FIG. 1C shows a zoom-in view of the temperature modulation assembly encircled 141 in FIG. 1B. FIG. 1D shows the temperature modulation assembly 140 with the cap and cover removed. FIG. 1D depicts the configuration and coupling of the underlying components housed within the temperature modulation assembly 140. An exploded view of the temperature modulation assembly 140 is shown in FIG. 1E, along with the other components of the temperature therapy device 101.

Referring to FIG. 1C, a plan view of the temperature modulation assembly 140 from FIG. 1B is presented, according to some embodiments. In some embodiments, the temperature modulation assembly 140 can include a cap 158 and cover 154. Also shown in FIG. 1C is the direction of the air flow used by the temperature modulation assembly 140 to regulate the temperature of the components housed within the temperature modulation assembly 140. In some embodiments, for air intake 131 into the temperature modulation assembly 140, air is pulled in though cap 158 by a fan into a heatsink, e.g., fan 154 and heatsink 152 shown below in FIG. 1D. In some embodiments, for airflow outtake 133 of the temperature modulation assembly 140, the fan pushes air through the heatsink, and out of the temperature modulation assembly 140 through vents 155 of the cover 154. Furthermore, although the air flow is shown in one direction in the example of FIG. 1C, e.g., intake 131 through the cap 158 and exhaust through the vents 155, the air can flow in the opposite direction. For example, air can flow into the temperature modulation assembly through the vents 155 and exit the temperature modulation assembly through the cap 158.

Referring to FIG. 1D, a plan view of the temperature modulation assembly from FIGS. 1B and 1C without the cover and cap is presented. The temperature modulation assembly 140 can include a spacer 148, a heatsink 152, and a fan 154. The spacer 148 can also be referred to as a mounting component, among other terms. FIG. 1D shows an exemplary mounting configuration of the fan 154 to the spacer 148. In an example, the fan 154 can be secured by screws 149 inserted into columnal structures 147 of the spacer 148. Although not shown, the screws 149 can also be located through corresponding holes within the cover 158 of FIG. 1C. In some embodiments, as shown, the heatsink 152 can be secured between the fan 154 and the spacer 148. In an example, the heatsink 152 can be secured by a clamping force between the fan 154 and the spacer 148.

Figure 1E:
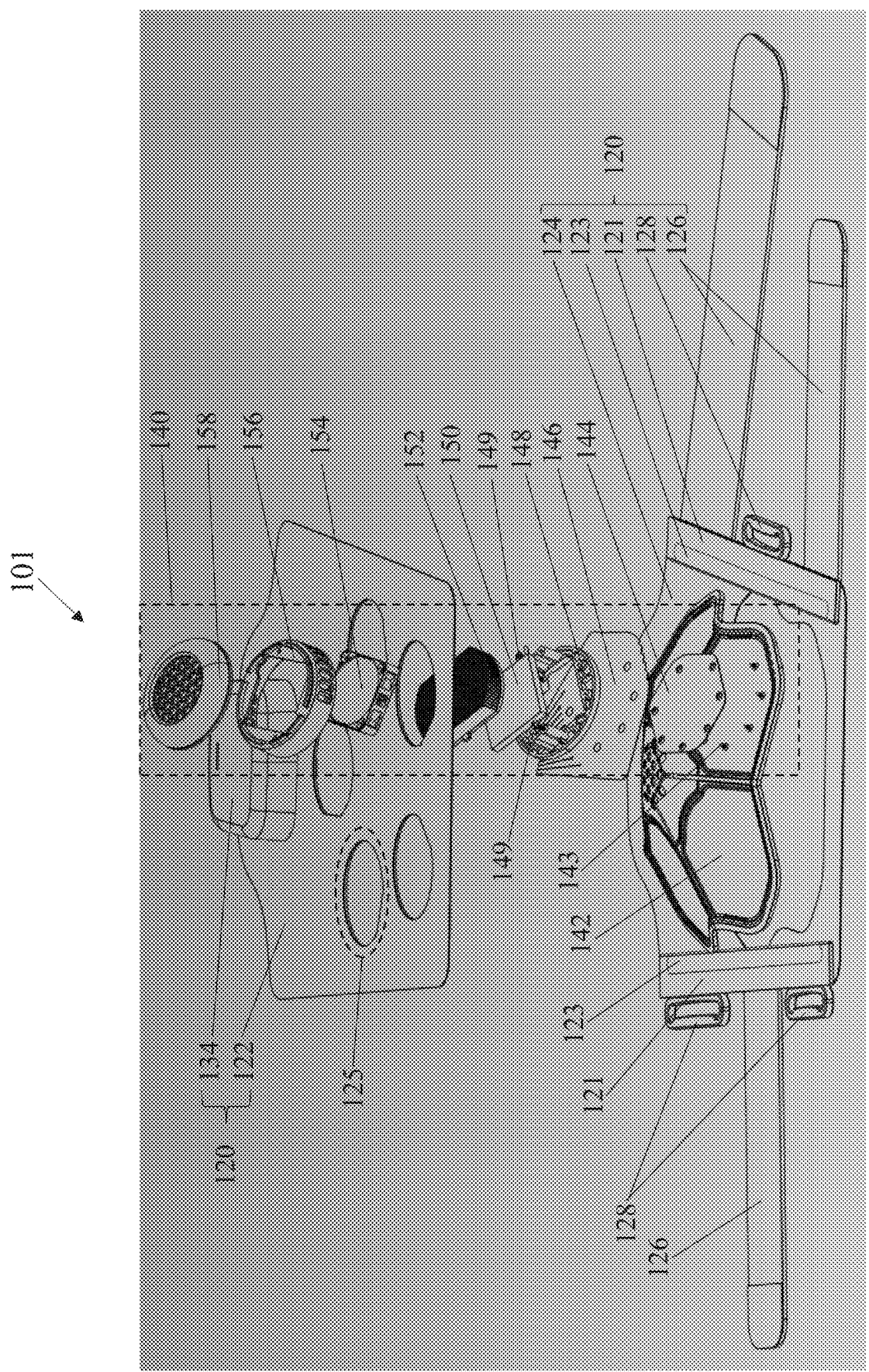
FIG. 1E illustrates an exploded view of the temperature therapy device, according to some embodiments.

Overview of a Temperature Therapy Device Including a Temperature Modulation Assembly and a Multi-Layer Retention Mechanism Referring to FIG. 1E, an exploded view of the temperature therapy device 101 of FIG. 1B including the temperature modulation assembly and multi-layer retention mechanism of FIGS. 1B-1D is presented, according to some embodiments.

Referring again to FIG. 1E, the temperature therapy device 101 can include a multi-layer retention mechanism 120 and a temperature modulation assembly 140, among other components. As shown, the multi-layer retention mechanism 120 can include a top layer 122 and a bottom layer 124. The top layer 122 of the multi-layer retention mechanism can include and/or be coupled to a control module 134, similar to that described with reference to FIG. 1B. The bottom layer 124 of the multi-layer retention mechanism can include and/or be coupled to one or more boning mechanisms 123, one or more structural support pieces 121, one or more straps 126 and one or more locking mechanisms 128, e.g., similar to those described with reference to FIG. 1B. Furthermore, the top layer 122 can include one or more openings 125, where the edges of the openings 125 can be configured to be received and/or secured by a spacer 148 and cover 156 of the temperature modulation assembly 140. In one example, the top layer 122 can include alignment features along edges of the openings 125 that are received by corresponding alignment features of the spacer 148 and the cover 156. The alignment features of the top layer 122 can be used for ensuring the spacer 148, top layer 122 and cover 156 are all correctly aligned and/or mounted together. In some embodiments, the top layer 122 and bottom layer 124 can include a flexible fabric. Therefore, the multi-layer retention mechanism can include the top layer 122, control module 134, bottom layer 124, one or more boning mechanisms 123, one or more structural support pieces 121, one or more straps 126 and one or more locking mechanisms 128.

Referring still again to FIG. 1E, in some embodiments, the bottom layer 124 can include and/or be coupled to a silicone overmold insert 142. In some embodiments, the silicone overmold insert 142 can be configured to receive one or more temperature modulation assemblies 140. In some embodiments, the silicone overmold insert 142 can be configured to be placed on a user's body part (e.g., a knee region, a lower back region, an elbow region, etc.).

Referring yet again to FIG. 1E, in some embodiments, although only one temperature modulation assembly 140 is shown in FIG. 1E, e.g., in exploded view, the temperature therapy device 101 can include more than one temperature modulation assembly. In an example, and as shown in FIG. 1B, the temperature therapy device 101 can include five temperature modulation assemblies. As also shown, the temperature modulation assembly 140 can be coupled to a portion of the silicone overmold insert 142 and/or a portion of the top layer 122. The temperature modulation assembly 140, is described in further detail below.

Referring again to FIG. 1E, in some embodiments, the temperature modulation assembly 140 can include a heat spreader 146 disposed between a mounting plate 144 and a spacer 148. In some embodiments, the mounting plate 144 can be configured to attach to the silicone overmold insert 142 on one side and to attach to the heat spreader 146 on another side. In an example, the mounting plate 144 can include an adhesive (e.g., a silicone adhesive) (e.g., a bottom surface of the mounting plate 144 can be coated with an adhesive) which can be configured to bond with a surface/layer of the silicone overmold insert 142. In some examples, the heat spreader 146 can include a primer layer (e.g., a bottom surface of the heat spreader 146 can be coated with a primer layer) that is configured to bond with an adhesive (e.g., another silicone adhesive) on another, opposite surface of the mounting plate 144 (e.g., the surface of the mounting plate facing the heat spreader 146). Additionally, the primer layer can also be configured to bond with an adhesive (e.g., a silicone adhesive) on a surface of the silicone overmold insert.

Referring again to FIG. 1E, in some embodiments, the spacer 148 can be positioned between the heat spreader 146 and heatsink 152. Additionally, a thermoelectric cooler (TEC) 150 can be located within a central opening of the spacer 148. The spacer 148 can also include at least one bottom opening and at least one on top opening located at a bottom portion and a top portion of the spacer 148, respectively. The bottom and top openings can be configured to receive respective screws 143/149 from the bottom and/or top of the spacer 148, respectively. In an example, at least one bottom screw 143 can be used to mount the mounting plate 144 and the heat spreader 146 to the bottom portion of the spacer 148, where the mounting plate 144 and heat spreader 146 can include corresponding mounting openings for the bottom screws 143. The openings through the heat spreader 146 can be aligned with the openings of the mounting plate 144. The heatsink 152 can be placed above the spacer 148. In some embodiments, the heatsink 152 can be disposed flush against a top portion of the spacer 148. Furthermore a fan 154 can be disposed over the heatsink 152 and the spacer 148. In some embodiments, the heatsink 152 is secured between the spacer 148 and the fan 154, e.g., the heatsink 152 can be clamped down by the spacer 148 and the fan 154. In some embodiments, at least one top screw 149 can be used to mount the fan 154 to the spacer 148 through at least one opening of the fan 154 and a corresponding top opening of the spacer 148. In an example, the at least one opening of the fan 154 can be aligned with at least one top opening of the spacer 144. Thus, in some embodiments, the heatsink 152 can be held between the fan 154 and spacer 148 by a force, e.g., a clamping pressure, between the fan 154 and the spacer 148 upon mounting the fan 154 to the spacer 148. The heatsink 152 can include an alignment feature that allows for an accurate placement of the heatsink 152 over the spacer 148. In an example, the alignment feature of the heatsink 152 can fit into a notch, e.g., corresponding alignment feature of the spacer 148, allowing for the heatsink 152 to lock in place along a horizontal direction.

Referring yet again to FIG. 1E, in some embodiments, a cover 156 and cap 158 can be placed over the spacer 148, heatsink 152, fan 154 and a portion of the top layer 122. In an example the cover 156 can secure the top layer 122 to the spacer 148. Furthermore, in some embodiments, the cover 156 can include one or more openings that can provide air circulation for the heatsink 152. In an example, the one or more openings can be referred to as vents. In some embodiments, the one or more vents in the cover 156 can be located along a wall portion of the cover 156. In some embodiments, the one or more vents of the cover 156 can be grouped into two groups of openings. In an example, one group of openings can be located at an opposite side from another group of openings along a wall portion of the cover 156. The temperature modulation assembly 140 can also include a cap 158. The cap 158 can be placed over the cover 156. The cap 158 can also include a locking mechanism that fits into a corresponding locking mechanism in the cover 156. In some embodiments, the cover 156 can go down to and meet a bottom portion of the fan 154. The cap 158 can include one or more openings, which can also be referred to as holes, slits or gaps on a top portion of the cap 158. In an example, the one or more openings at the top portion of the cap 158 can be in the shape of a hexagon and/or arranged in a honeycomb configuration. In some embodiments, the temperature modulation assembly 140 can be configured to draw air through the openings in the cap 158, by the fan 154, and air can be pushed to a central portion of the heatsink 152, where the air exits the temperature modulation assembly 140 out through one or more vents of the cover 156 (e.g., as described with reference to FIG. 1C).

Components of a Temperature Therapy Device

Each component of the temperature therapy device in FIGS. 1B-1E is described in detail below, according to some embodiments. For example, the mounting plate 124 of FIG. 1E is described in detail with reference to FIGS. 2A-2D. In another example, the heat spreader 126 of FIG. 1E is described in detail with reference to FIGS. 3A and 3B.

Figure 2A:
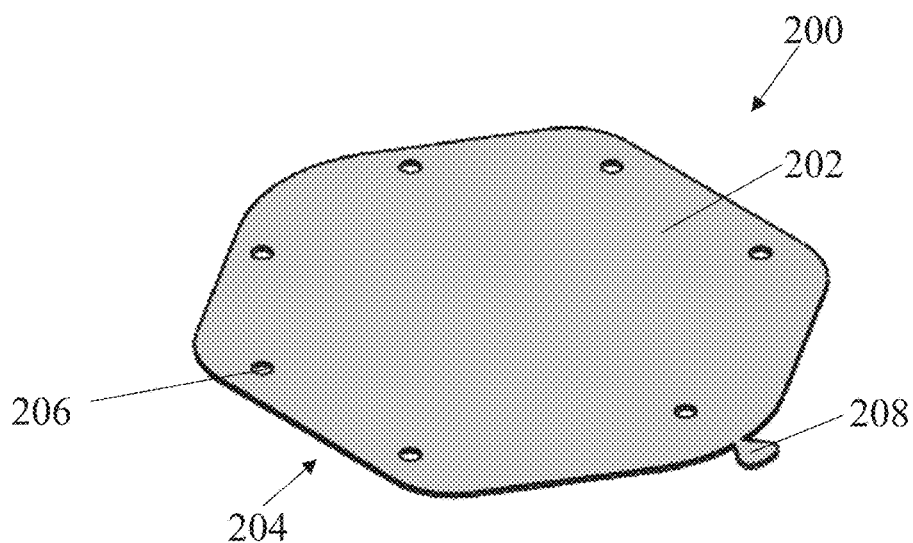
FIG. 2A illustrates a top view of a mounting plate of the temperature modulation assembly, according to some embodiments.
Figure 2B:
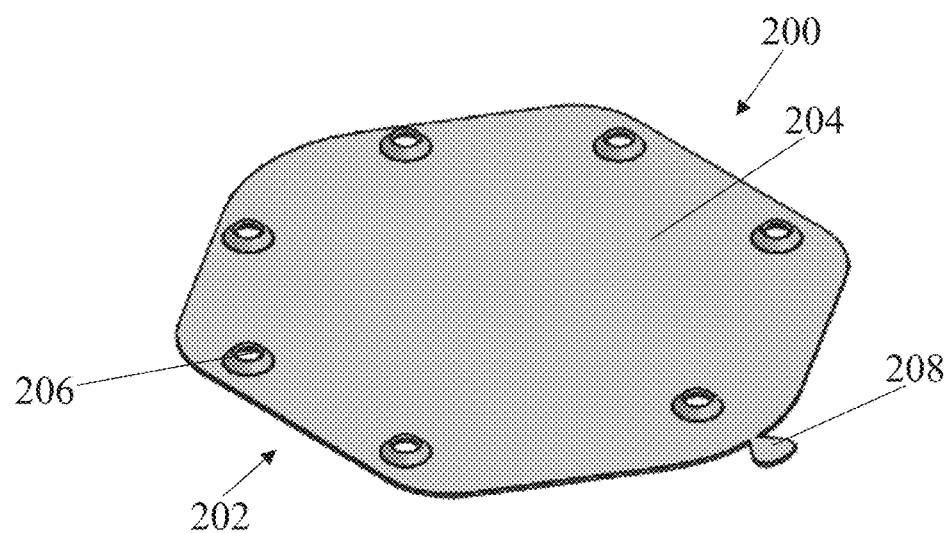
FIG. 2B illustrates a bottom view of the mounting plate, according to some embodiments.
Figure 2C:
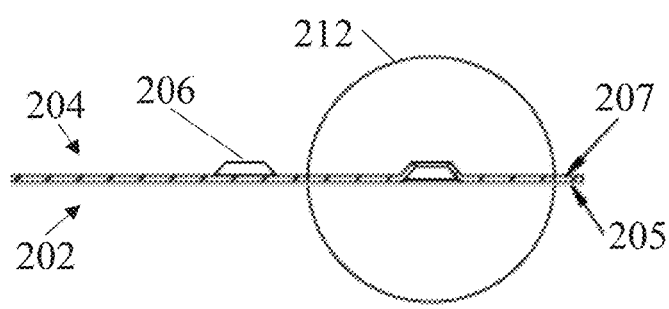
FIG. 2C illustrates a cross-sectional view of the mounting plate, according to some embodiments.
Figure 2D:
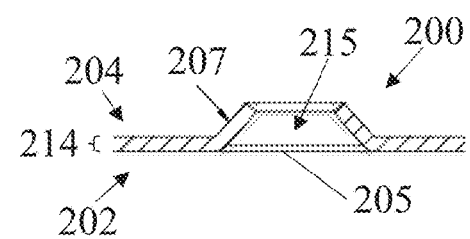
FIG. 2D illustrates a zoom-in view of an opening of the mounting plate, according to some embodiments.

Referring to FIGS. 2A-2D, various views of a mounting plate of the temperature modulation assembly are shown, according to some embodiments. FIG. 2A shows a top view and 2B shows a bottom view of the mounting plate of the temperature modulation assembly. FIG. 2C shows cross-sectional view of the mounting plate and FIG. 2D illustrates a zoom-in view of an opening of the mounting plate.

Referring to FIGS. 2A and 2B, a top view and a bottom view of a mounting plate of the temperature modulation assembly are presented respectively, according to some embodiments. As shown, the mounting plate 200 can have a top portion 202 and a bottom portion 204. FIG. 2A shows the mounting plate 200 from a top view, e.g., showing the top portion 202 of the mounting plate 200. FIG. 2B shows the mounting plate from a bottom view, e.g., showing the bottom portion 204 of the mounting plate 200. In some embodiments, the mounting plate 200 can include one or more openings 206. In some embodiments, the one or more openings 206 can be configured to receive one or more screws that can be used to mount the mounting plate 200 to a heat spreader and a spacer. In some embodiments, the mounting plate 200 can be cut into any suitable shape: circular, oval, polygonal, among other shapes. In an example, the mounting plate 200 can be in hexagonal shape as shown in FIGS. 2A and 2B. The mounting plate 200 can also include a tab feature 208. In an embodiment, the tab feature 208 can be in any shape: a triangular, circular, square, among other shapes. In an example, the tab feature 208 can be in a teardrop shape as shown. In some embodiments, the mounting plate 200 can include aluminum (e.g., anodized aluminum, 6061 aluminum, etc.). In some embodiments, the aluminum used in the mounting plate 200 is untreated, e.g., the aluminum is not anodized. In some embodiments, the mounting plate 200 can include any metal and/or alloy, for example, copper, steel, among other metals.

Referring to FIGS. 2C and 2D, respectively, a cross-sectional view of the mounting plate and a zoom-in view of an opening of the mounting plate are presented, according to some embodiments. In the views of FIGS. 2C and 2D, the top portion 202 of the mounting plate 200 is shown facing downward. In some embodiments, the mounting plate 200 can include a first adhesive 205 disposed over (e.g., on) a top portion 202 of the mounting plate 200. In some embodiments, the first adhesive 205 can include or be a double sided tape. In an example, the first adhesive 205 can include an acrylic on one side and a silicone adhesive on another side. In some embodiments, the acrylic side of the first adhesive 205 can be facing the top portion 202 of the mounting plate 200 and the silicon adhesive side can be facing a silicone overmold insert, e.g., the silicone overmold insert 142 in FIG. 1E. In an example, the first adhesive 205 can include 3M™ tape 9731. In some embodiments, a peel off liner can be disposed over the first adhesive 205 to protect it during manufacturing. A second adhesive 207 can be disposed over (e.g., on) the bottom portion 204 of the mounting plate 200. In some embodiments, as shown in FIG. 1E, the bottom portion 204 of the mounting plate 200 can be coupled to the heat spreader 146 of FIG. 1E via the second adhesive 205. In an example, the second adhesive 205 can support adhering the mounting plate 200 to the heat spreader. A zoom-in view of an opening 212 from FIG. 2C is shown in FIG. 2D. Referring to FIG. 2D, in some embodiments, the mounting plate 200 can have a thickness 214 in a range of 0.2 mm to 1 mm. In an example, the mounting plate 200 can have a thickness 214 of approximately 0.40 mm. As shown in FIG. 2D, the first adhesive 205 can be disposed over the opening 212 (e.g., representative of the openings 206), where a gap 215 can be disposed between the opening 206 and the first adhesive 205. In some embodiments, the mounting plate 200 can be configured to anchor and/or stabilize the temperature modulation assembly 140 of FIGS. 1A-1E. Additionally, when mounted together with the rest of the temperature modulation assembly components, the bottom portion 204 of the mounting plate 200 can be facing up toward a bottom portion of the heat spreader, as shown in FIG. 1E and further described below.

Figure 3A:
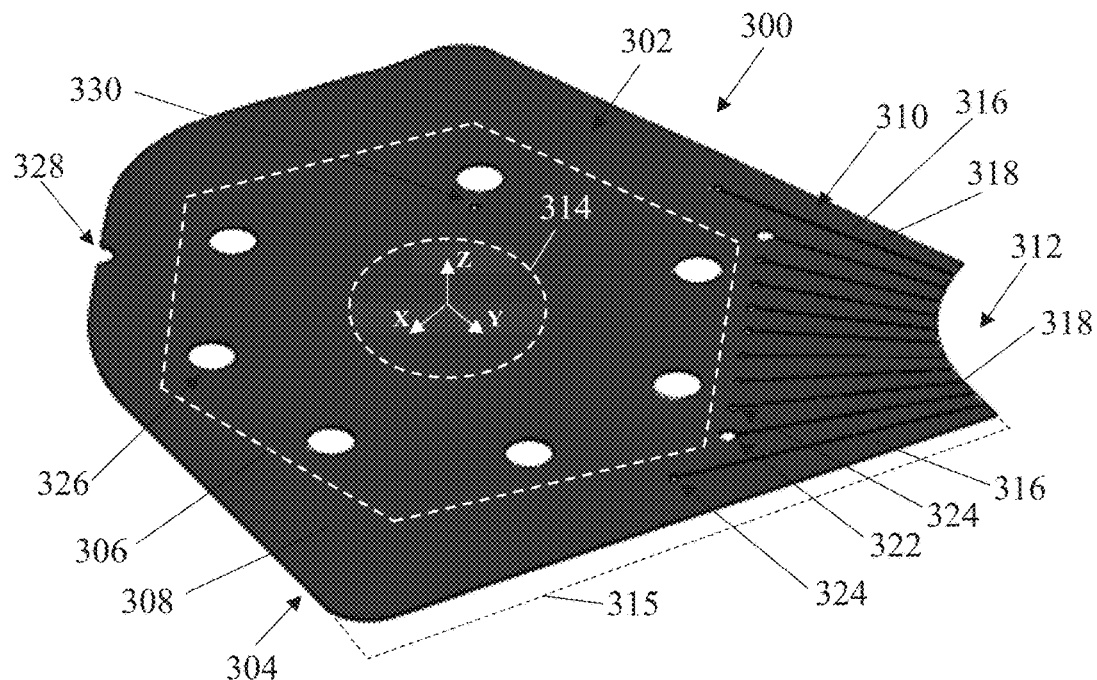
FIG. 3A illustrates a heat spreader of the temperature modulation assembly, according to some embodiments.
Figure 3B:
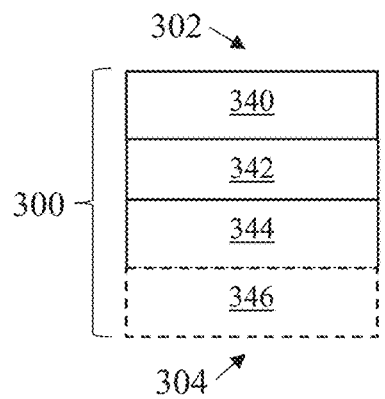
FIG. 3B illustrates a block diagram of a cross-section of the heat spreader, according to some embodiments.

Referring to FIGS. 3A and 3B, various views of a heat spreader of the temperature modulation assembly are shown, according to some embodiments. FIG. 3A show a heat spreader of the temperature modulation assembly. FIG. 3B shows a cross-sectional view of the heat spreader.

Referring to FIG. 3A, a heat spreader of the temperature modulation assembly is presented, according to some embodiments. The heat spreader 300 can have a top portion 302 and a bottom portion 304. An inner region 306 of the bottom portion 302 of the heat spreader 300 can be coupled to the bottom portion 204 of a mounting plate (e.g., the mounting plate 200 of FIGS. 2A-2D). When mounted together, at the inner region 306, the bottom portion 304 of the heat spreader 300 can be coupled to the bottom portion 204 of the mounting plate 200. In some embodiments, the heat spreader 300 can be configured to spread temperature in a horizontal and vertical direction, e.g., along x-, y- and z-directions. In an embodiment, the heat spreader 300 can be configured to provide for an efficient application of heat, which can enable the temperature therapy device to deliver desired amounts and/or rates of hot or cold therapy using fewer TECs than would otherwise be required. In some embodiments, the heat spreader 300 can arrive as a roll at the beginning of a manufacturing process. In some embodiments, during manufacturing, the bottom portion 304 of the heat spreader 300 can include a liner which can later be removed to expose the adhesive disposed at the bottom portion 304 of the heat spreader 300.

Referring again to FIG. 3A, the heat spreader 300 can include one or more fingers 310 extending from one end 312 of the heat spreader 300. In one example, there can be 11 fingers 310 formed at one end 312 of the heat spreader 300. In some embodiments, at least one finger 310 can extend from one side 312, e.g., a tapered side, of the heat spreader 300 toward a central portion 314 of the heat spreader. The fingers 310 can be cuts (e.g., narrow, elongated gaps) in the heat spreader material itself. In some embodiments, the fingers 310 can be configured to provide mechanical stress relief and/or strain relief when the temperature therapy device is in use. In an embodiment, the average length of a finger 310 can be less than or equal to ½ and/or ¼ of the length of a side 315 of the heat spreader 300. In some embodiments, the lengths of the fingers 310 can be in a range of approximately 5-25 mm. In one example, the lengths of the fingers 310 can be in a range of approximately 10-20 mm (e.g., 10-15 mm). In some embodiments, the lengths of the fingers 310 are selected to provide as much surface area of the heat spreader as possible around a user's knee. In some embodiments, the one or more fingers 310 can include longer fingers 316 at an outer portion and shorter fingers 318 at an inner portion of the heat spreader 300. In some embodiments, the fingers 310 can include one or more openings 322, 324 at one end of each finger 310. In an embodiment, the openings 322, 324 can vary in size. In an example, one opening 324 at one end of one finger can have a diameter which is less than a diameter of another opening 322 at an end of another finger. In some embodiments, the openings can be configured to relieve mechanical stress from the fingers and/or at the one end 312 of the heat spreader 300.

Referring still to FIG. 3A, the heat spreader 300 can have one or more openings 326. The one or more openings 326 can be aligned with corresponding openings 206 of the mounting plate 200 from FIGS. 2A-2D. In some embodiments, the one or more openings 326 can be configured to receive one or more screws that can be used to mount the mounting plate 200 and heat spreader 300 to the spacer 148 of FIG. 1E.

Referring yet again to FIG. 3A, the heat spreader 300 can include a notch 328. In an example, the notch 328 can be used to help an operator determine which temperature modulation assembly to attach to a corresponding heat spreader during manufacturing or fabrication. In an example, although one heat spreader is shown, as described herein, multiple, e.g., different/unique, heat spreaders and/or multiple, e.g., different/unique, temperature modulation assemblies can be used. In some embodiments, a heat spreader 300 can have one or more notches. Each individual notch or group of notches can be different and/or unique from one another. In an example, as shown, the heat spreader 300 can include one notch 328. In another example, another heat spreader corresponding to another temperature modulation assembly can have two notches. In still another example, another heat spreader corresponding to another temperature modulation assembly can have three notches, and so on. Therefore, in some embodiments, the number of notches can determine which temperature modulation assembly is to be coupled to a corresponding heat spreader. For example, a first temperature modulation assembly can be mounted to the heat spreader 300 that includes the single notch 328, a second temperature modulation assembly can be mounted to another heat spreader that includes two notches, and so on. In some embodiments, there can be one to five notches, e.g., corresponding to up to five temperature modulation assemblies. As described above, in some embodiments, a temperature therapy device can include one or more, e.g. greater than five, temperature modulation assemblies. Furthermore, in some embodiments, the notch 328 can correspond to the notch 1140 of the silicone overmold insert 1120 of FIGS. 11A-11D. In an example, the notches of one or more, e.g., different/unique, heat spreaders can be shaped to fit into and/or align to corresponding notches of the silicone overmold insert of FIGS. 11A-11D.

Referring still again to FIG. 3A, the heat spreader 300 can include an alignment opening 330. In an embodiment, the alignment opening 330 can be located adjacent to at least one mounting opening 326. In some embodiments, the alignment opening 330 can correspond to a bottom alignment feature 533 of the spacer 500 (e.g., referring to FIG. 5C). In an example, the alignment opening 330 and bottom alignment feature 533 can be used to help an operator determine the proper alignment and/or placement between the spacer 500 and the heat spreader 300 during manufacturing and/or fabrication of a temperature modulation assembly. In an example, the bottom alignment feature 533 can fit into and/or align to the alignment opening 330.

Referring to FIG. 3B, a cross-section of the heat spreader is illustrated, according to some embodiments. In some embodiments, the heat spreader 300 can include 3 layers (340, 342, 344). In an example, the heat spreader can include a top layer 340, a middle layer 342 and a bottom layer 344. In some embodiments, the top layer 340 can be or include a first adhesive layer, the middle layer 342 can be or include a graphite/graphene layer and the bottom layer 346 can be or include a second adhesive layer. In some embodiments, the first adhesive layer and/or second adhesive layer can include a silicone adhesive. In some embodiments, the top layer 340 and/or bottom layer 344 can have a thickness in a range of approximately 8-12 micrometers. In some examples, the top layer and/or bottom layer can have thickness of approximately 10 micrometers. In some embodiments, a PET (polyethylene terephthalate) layer can be disposed over the top layer 340 and/or bottom layer 344. In an example, the middle layer 342 can include a graphene layer which includes a synthetic graphite sheet. In some examples, the middle layer 342 can include small particles (e.g., of graphene). In some embodiments, the graphene layer can include a metal based powder for thermal energy transfer. In an example, the heat spreader 300 can include DSN5050-10DC10SB Synthetic Graphite Sheet from DASEN company.

Referring again to FIG. 3B, in some embodiments, a primer can be applied to the heat spreader. As shown, the primer 346 can be applied to the bottom layer 344 of the heat spreader 300. In some embodiments, applying the primer to the bottom layer 344 forms a primer layer 346 over the bottom layer 344. In some embodiments, the primer can be mixed with a catalyst, and subsequently applied (e.g., evenly spread) over the bottom layer 344 of the heat spreader 300. In an example, the primer can act as another layer disposed directly on the bottom layer 344. In some embodiments, in contrast to that shown in FIG. 3B, the primer can be applied to the top layer 340 of the heat spreader 300 rather than being applied to the bottom layer 344. In some embodiments, the primer can be applied to both the bottom layer 344 and the top layer 340 of the heat spreader. In some embodiments, the primer can be applied immediately after mixing with the catalyst. In an example, a ratio of 30:1 between the primer to the catalyst can be used. In some embodiments, the primer can be diluted using toluene. In some embodiments, a thin clothe and/or a latex glove can be used to apply the primer to the bottom layer 344 and/or top layer 340 of the heat spreader 300. In an example, the inventors found a cloth and/or a latex glove to be an effective application tool in comparison to a brush, where the brush can create markings, e.g., brush marks, on the primer after application. In some embodiments, the primer can be applied with a thickness of approximately 1 mm. In some embodiments, the entire bottom portion 304 and/or top portion 302 of the heat spreader can be covered by respective layers of the primer 346.

Referring still to FIG. 3B, subsequent to the mixing the primer with the catalyst and application of the primer to the bottom layer and/or top layer, the primer can be allowed to dry. In some embodiments, the primer can be allowed to dry for approximately 10-20 minutes. In some embodiments, once the primer is dry, the primer can be allowed to cure for any suitable amount of time before applying and/or adhering the mounting plate to the heat spreader 300. In some embodiments, the primer can be configured to allow the silicon adhesive on the mounting plate to uniformly adhere to the e.g., the first or third layers 340, 344 of the heat spreader 300. In some embodiments, the primer can include a SilGrip PSA529 Silicone Pressure Sensitive Adhesive by Momentive.

Referring to FIGS. 1E, 3A, 3B and FIGS. 2A-2D, in some embodiments, the primer layer 346 can be used to couple the heat spreader 300 to a mounting plate (e.g., the mounting plate 200 of FIGS. 2A-2D) and to a silicone overmold insert (e.g., the silicone overmold insert 142 of FIG. 1E). In an example, a silicone based adhesive disposed on the mounting plate 200 can be coupled directly to the primer layer 346. In some examples, the inner region 306 of the bottom portion 302 of the heat spreader 300 can be coupled to the bottom portion 204 of the mounting plate 200 via the primer layer 346 and via the silicone adhesive over the mounting plate 200. In a similar manner, in some embodiments, the heat spreader 300 can be coupled to the silicon overmold insert 142 at regions of the bottom portion 304 outside of the inner region 306 via a silicone adhesive on the silicone overmold insert 142 and via the primer layer 346. Therefore, in a same embodiment, the primer layer 346 can enable the coupling between the heat spreader 300, mounting plate 200 and silicon overmold insert 142 via the primer layer 346 and a silicone adhesive disposed over the mounting plate 200 and a silicone adhesive disposed over the silicone overmold insert 142. In specific example, the primer 346 can be configured to uniformly bond the heat spreader 300 to the mounting plate 200 and/or to the silicone overmold insert 142. In some embodiments, the configuration described above which is allows the heat spreader 300 and/or mounting plate 200 to bond to the silicone overmold insert 142 (e.g., silicone substrate) can be referred to as system for mounting rigid components to a silicone substrate for a temperature therapy device.

Figure 4:
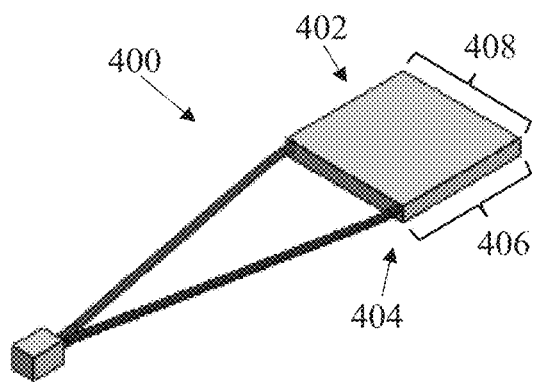
FIG. 4 illustrates a thermoelectric cooler (TEC) of the temperature modulation assembly, according to some embodiments.

Referring to FIG. 4, a thermoelectric cooler (TEC) of the temperature modulation assembly is presented, according to some embodiments. In an embodiment, a TEC 400 can be selected based on its thermal conductivity rating. In an example, a TEC 400 having a high thermal conductivity rating, e.g., greater than or equal to the thermal conductivity of a ceramic material, can be used. The TEC 400 can have a top portion 402 and a bottom portion 404. In some embodiments, the length 406 of the TEC can be approximately equal to its width 408. In an example, the TEC 400 can be 40 mm in length 406 and 40 mm in width 408. A thermal grease can be disposed between a heat spreader and the TEC 400, e.g., referring to the configuration shown in FIG. 1E. In an example, a thermal grease with a high thermal conductivity, e.g., in the range of approximately 1-15 w/mk (for example, 1 w/mk), can be used. In an embodiment, a thermal grease from Halnziye company can be used.

Figure 5A:
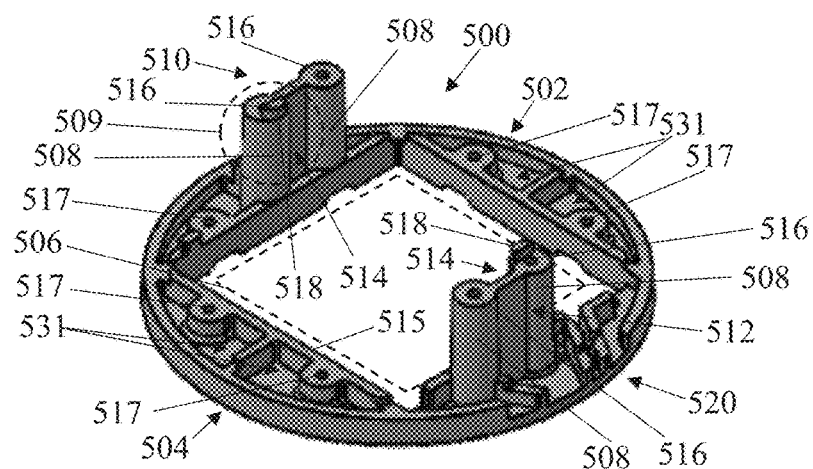
FIG. 5A illustrates a spacer of the temperature modulation assembly, according to some embodiments.
Figure 5B:
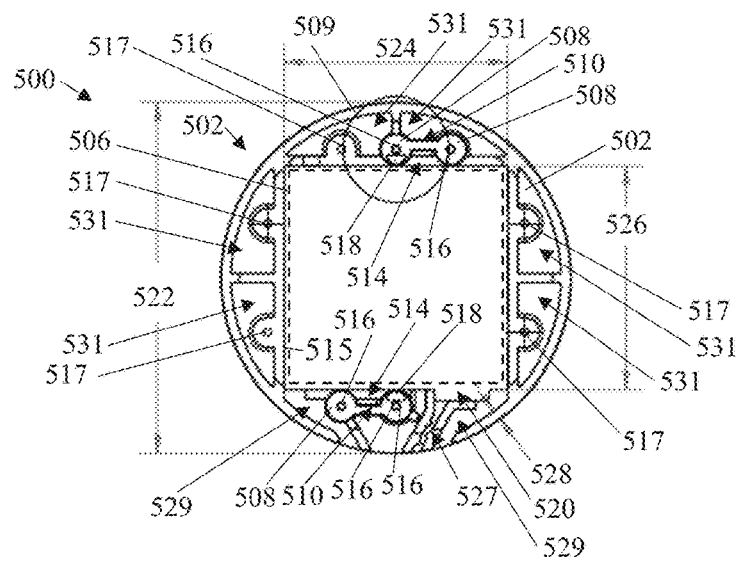
FIG. 5B illustrates a top view of the spacer, according to some embodiments.
Figure 5C:
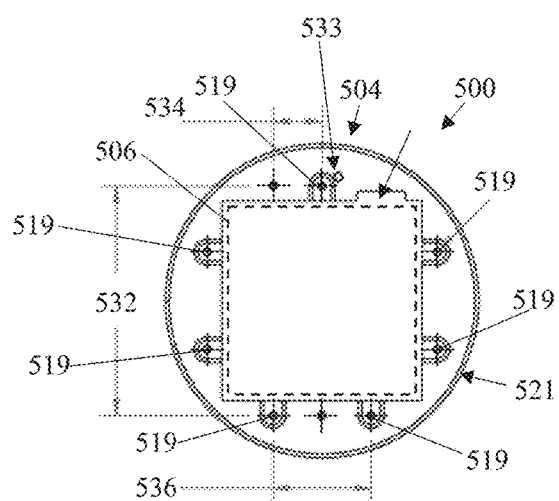
FIG. 5C illustrates a bottom view of the spacer, according to some embodiments.
Figure 5D:
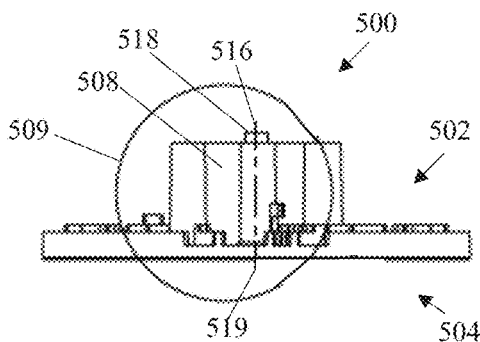
FIG. 5D illustrates a side view of the spacer, according to some embodiments.

Referring to FIGS. 5A-5D, various views of a spacer are shown, according to some embodiments. In some embodiments, a spacer can include a mounting system for connecting elastic/flexible portions of the temperature therapy device to inelastic, hard and/or solid elements. In an example, the spacer can include various mechanical features that are configured to mount/connect hard or solid elements to flexible objects. In one example, the spacer can also be called a mounting system. FIG. 5A illustrates a spacer of the temperature modulation assembly. FIG. 5B illustrates a top view of the spacer. FIG. 5C illustrates a bottom view of the spacer. FIG. 5D illustrates a side view of the spacer.

Referring to FIGS. 5A and 5B, multiple views of the spacer are presented, according to some embodiments. In some embodiments, the spacer 500 can include a top portion 502 and a bottom portion 504. In some embodiments, the spacer 500 can include a central opening 506 configured to receive a TEC (e.g., the TEC from FIG. 1E and FIG. 4). In some embodiments, the central opening 506 can include dimensions 524, 526 that allow the TEC to fit into the central opening 506. In an example, the central opening 506 can have a length 524 in a range of approximately 30-60 mm and width 526 in a range of approximately 30-60 mm. In some embodiments, the central opening 506 can include a shape a similar to and/or the same shape as the TEC, e.g., a square opening. Although the central opening 506 can include a square opening, other shapes can be used such as a circular opening, polygonal opening, among others. As shown, the spacer 500 can have an outer diameter 522 in a range of approximately 50-70 mm. In some embodiments, the spacer 500 can have an outer wall 528. In some embodiments, the outer wall 528 can have a thickness in the range of approximately 0.5-2.5 mm.

Referring again to FIGS. 5A and 5B, in some embodiments, the spacer 500 can include one or more columnal structures 508 extending from the top portion 502 of the spacer 500. As referred to herein, the one or more columnal structures 508 can be referred to as columnal structures or a plurality of columnal structures. In an example, the spacer 500 can include four columnal structures 508. An exemplary columnal structure is encircled in 509 of FIGS. 5A and 5B. In some embodiments, a pair of columnal structures 510, 512 can be used, e.g., one pair on either side of the spacer 500 as shown in FIGS. 5A and 5B. In an example, a first pair of columnal structures 510 and a second pair of columnal structures 512 are shown in FIGS. 5A and 5B. In some embodiments, the spacer 500 can include a notch 514. In an embodiment, the notch 514 can be configured to align the placement of a heatsink over the spacer 500 and secure the heatsink within the temperature modulation assembly (e.g., the heatsink 152 from FIG. 1E). In some embodiments, the notch 514 can be located between to columnal structures of a pair of columnal structures 510, 512, as shown in FIGS. 5A and 5B. In some embodiments, one or more notches 514 can be used. In an example, provided two pairs of columnal features 510, 512, there can be two corresponding notches, one for each per pair of columnal structures. In some embodiments, as shown in FIG. 1E, a heatsink can be placed over the spacer 500. In some embodiments, a tab of the heatsink (e.g., FIGS. 6A-6C) can be aligned and/or placed into the notch 514 when positioning the heatsink over the spacer 500. In some embodiments, the notch 514 and tab of the heatsink can hold the heatsink in place over the spacer 500, resisting any movement of the heatsink. In an example, the notch 514 and tab combination can lock and/or hold the heatsink in place along a horizontal direction between the pairs of columnal structures 510, 512 of the spacer. In some embodiments, the heatsink can include one or more tabs. In an example, the heatsink can have two tabs and the two tabs can align with, and be placed into, two corresponding notches 514 of the spacer 500, e.g., the two notches 514 shown in FIGS. 5A and 5B. In some embodiments, one or more notches 514 can be configured to keep heatsink from twisting in place and maintain a desired heatsink orientation, e.g., maintain direction or alignment of heatsink fins during and after assembly of the temperature therapy device.

Referring still to FIGS. 5A and 5B, in some embodiments, each columnal structure 508 can include a top opening 516 configured to receive a screw to be inserted from the top portion 502 of the spacer 500. In some embodiments, the columnal structures 508 can be configured to receive a screw for mounting a fan. In an example, the columnal structures 508 can be configured to receive a screw for mounting the fan from FIGS. 1 and 7. In an example, a screw can be placed through a corresponding opening in the fan and into a top opening 516. In some embodiments, one or more top openings 516 can be used. In an example, there can be a top opening 516 corresponding to each columnal structure 508. In some embodiments, a top alignment feature 518 can be located at a top end of one or more columnal structures 508 next to the top opening. In some embodiments, the top alignment feature 518 can be configured to ensure that an operator inserts a screw in a top opening 516 in the correct direction and/or configuration. In example, an operator can refer to the top alignment feature 518 when placing a screw in a top opening 516 for mounting the fan. In some embodiments, not all columnal structures 508 can include a top alignment feature 518. In an example, only columnal structures 508 which are used for mounting a fan can include a top alignment feature 518. In an embodiment, an operator can be instructed to locate the top alignment feature 518 and only place a screw (e.g., for mounting a fan) where the top alignment feature 518 is located. In some embodiments, the alignment features 518 located on a first pair of columnal structures 510 may not be aligned with another alignment feature 518 located on a second pair of columnal featured 512. In an example, an alignment feature 518 can be located on a first columnal structure of the first pair of columnal structures 510 and another alignment feature 518 can be located on a second, different, columnal structure of the second pair of columnal structures 512 as shown in FIGS. 5A and 5B. In an embodiment, the top alignment feature 518 can include various shapes. In some embodiments, the top alignment feature 518 can have various shapes such as circular, square, rectangular, oblong, polygonal, among others. In an example, as shown in FIGS. 5A and 5B, the top alignment feature 518 can include a half circle and/or half-moon shape. Thus, in some embodiments, the top alignment feature 518 can be configured to assist an operator in the location and/or placement of a fan. In some embodiments, the fan can be mounted over the heatsink and spacer using one or more screws to keep the heatsink in place, e.g., as described above. For example, during assembly of the mounting system, the heatsink can move and/or twist. Thus, in an example, the fan can be mounted over the heatsink and the spacer such that the heatsink is held in place by the fan. In the same example, the fan can keep the heatsink in place and prevent the heatsink from moving during and after assembly of temperature modulation assembly. In some embodiments, not all top openings 516 may correspond or be located at a columnal structure 508. In an example, some top openings 517 can be located on lower sides of the top portion 502.

Referring yet again to FIGS. 5A and 5B, in an embodiment, the spacer 500 can include one or more wire management features. In an example, the spacer 500 can include wire management features configured to receive at least one wire from a temperature sensor, TEC and/or fan (e.g., from FIG. 1E). In some embodiments, the wire management features can include ravines, wells, burrs and/or cut-outs built into the spacer 500 that include the dimensions of the wires for the electronics, e.g., from the temperature sensor, TEC and/or fan. In an example, the wire management features can be configured to receive one or more wires and can secure the wires in place during and after assembly of the temperature therapy device. In an embodiment, the spacer 500 can include a first wire management feature 527 that is configured to receive and secure one or more wires from a TEC. In an embodiment, the spacer 500 can include a second wire management feature 529 that is configured to receive and secure one or more wires from a fan. In an example, the wire management feature 529 for the fan can act like a hook and hold the wires from the fan in place.

Referring again to FIGS. 5A and 5B, in an embodiment, the spacer 500 can include one or more receiving features for various elements of the temperature modulation assembly. In some embodiments, the spacer 500 can include a receiving portion in a form of a cut-out 520 for a temperature sensor. In an example, the temperature sensor can be coupled to the TEC and the temperature sensor can fit into the cut-out 520 of the spacer 500. The spacer 500 can include a plurality of receiving portions 531, e.g., which also can be referred to as channels, to receive corresponding alignment features 1016 of the top layer as described in FIGS. 10A-10D below. Also, the spacer 500 can include an edge 515 adjacent to the alignment features 531. In some embodiments, the edge 515 of the spacer 500 can be aligned to a flat edge 1017 of the alignment feature 1016 of the top layer in FIGS. 10A-10D.

Referring to FIG. 5C, a bottom view of the spacer is presented, according to some embodiments. In some embodiments, the spacer 500 can include one or more bottom openings 519 located at the bottom portion 504 of the spacer 500, the bottom openings 519 can be configured to receive screws from the bottom portion 504 of the spacer 500. In some embodiments, the mounting plate from FIG. 1E and FIGS. 2A-2D can be mounted to the bottom portion 504 of the spacer 500 by inserting one or more screws through the bottom openings 519 in the spacer 500 and corresponding openings in the mounting plate. In some embodiments, the spacer 500 can include 7 bottom openings 519. In an example, the sum of the bottom openings 519 can add up to an odd number, e.g., the number of bottom openings 519 are not designed to be symmetric or even. In some embodiments, the bottom openings 519 can have an asymmetrical configuration. In an embodiment, the asymmetrical configuration of the bottom openings 519 can ensure that the mounting plate is mounted in a particular order, e.g., to prevent an operator from mounting the mounting plate incorrectly or opposite to the intended configuration. In some embodiments, the bottom portion 504 of the spacer 500 can have embossed and/or chamfered edges 521. In some embodiments, the edges 521 of the bottom portion 504 can be configured to receive and/or align to the edges of the mounting plate. In some embodiments, the distance between opposite bottom openings 532 can be in a range of approximately 30-60 mm. In some embodiments, the distance between adjacent bottom openings 534, 536 can be in a range of approximately 5-30 mm.

Referring again to FIG. 5C, in some embodiments, the spacer 500 can include a bottom alignment feature 533. In some embodiments, the bottom alignment feature 533 can be located adjacent to at least one bottom opening 519. In some embodiments, the bottom alignment feature 533 can correspond to an alignment opening 330 of the heat spreader 300 (e.g., of FIGS. 3A and 3B). In an example, the bottom alignment feature 533 and alignment opening 330 can be used to help an operator determine the proper alignment and/or placement between the spacer 500 and the heat spreader 300 during manufacturing and/or fabrication of a temperature modulation assembly. In an example, the bottom alignment feature 533 can fit into and/or align to the alignment opening 330.

Referring to FIG. 5D, a side view of the spacer is presented, according to some embodiments. A cross-sectional view of the columnal structures 508 from FIGS. 5A and 5B is shown in FIG. 5D. As shown, an exemplary columnal structure is encircled in 509 of FIG. 5D. Also, a side view of the top alignment feature 518 is shown in FIG. 5D. Additionally, FIG. 5D shows that the top opening can 516 extend through the spacer and meet a corresponding bottom opening 519. In some embodiments, each of the top openings 516 can have a corresponding bottom opening 519 e.g., from FIGS. 5A-5D. In some embodiments each of the top and bottom openings can 516, 519 be a through-hole, e.g., the openings can extend from the top opening 516, through the spacer 500 and out through a corresponding bottom opening 519.

Referring still again to FIGS. 5A-5D, in some embodiments, the spacer can include a material such as a plastic, resin and/or fireproof plastic/resin, among other materials. In an example, the spacer can include a material selected from the group consisting of Nylon 66, Dupont 801, and Dupont 2801.

Figure 6A:
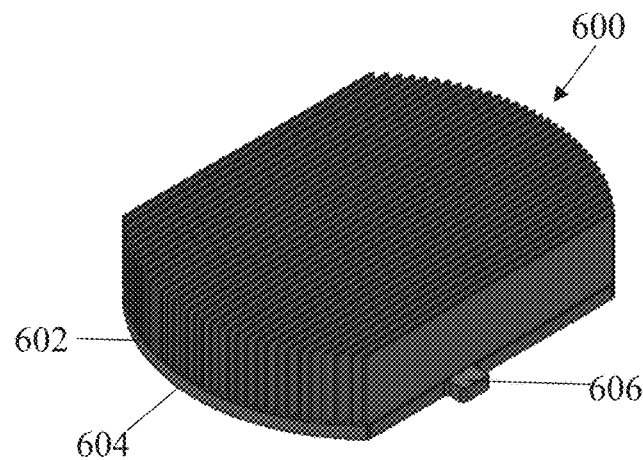
FIG. 6A illustrates a heatsink of the temperature modulation assembly, according to some embodiments.
Figure 6B:
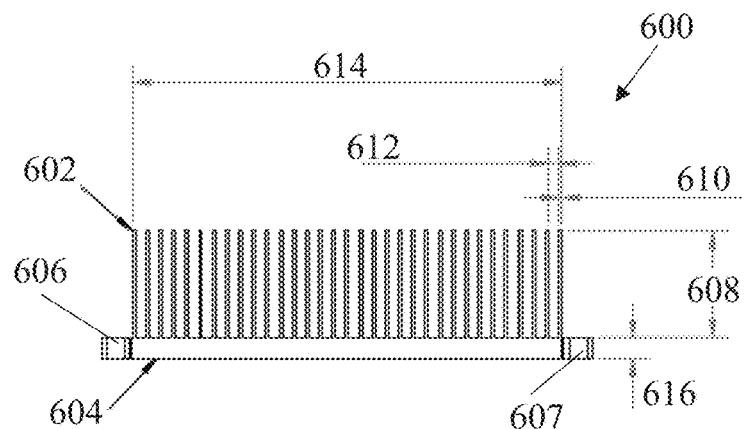
FIG. 6B illustrates a cross-sectional view of the heatsink, according to some embodiments.
Figure 6C:
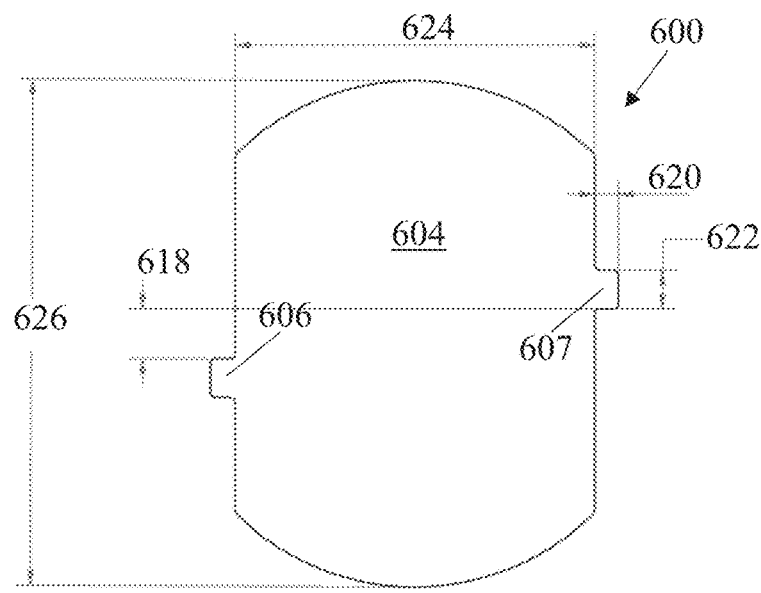
FIG. 6C illustrates a bottom view of the heatsink, according to some embodiments.

Referring to FIGS. 6A-6C, various views of a heatsink are shown, according to some embodiments. In some embodiments, the heatsink can include a component and/or material configured to draw heat away the TEC and/or other elements of the temperature modulation assembly. FIG. 6A illustrates a heatsink of the temperature modulation assembly. FIG. 6B illustrates a cross-sectional view of the heatsink. FIG. 6C illustrates a bottom view of the heatsink.

Referring to FIG. 6A, a heatsink is presented, according to some embodiments. In some embodiments, the heatsink 600 includes a plurality of fins 602 extending from a base portion 604 of the heatsink 600. In some embodiments, the plurality of fins 602 can be formed through a skiving technique. In some embodiments, the plurality of fins 602 can be referred to as skived fins. In some embodiments, in contrast to using extrusion which is one way conventional heatsinks are formed, the entire heatsink 600 can be formed using a skiving technique. In some embodiments, the heatsink 600 can be referred to as a skived heatsink. In an example, a metal work skiving process can be used to form heatsink 600 and/or the plurality of fins 602. As referred to herein the plurality of fins 602 can also be referred to individually, e.g., each fin 602 or as one or more fins 602. In some embodiments, the heatsink 600 can include a first tab 606. In some embodiments, one or more tabs can be used as shown in FIGS. 6B and 6C.

Referring to FIG. 6B, a cross-sectional view of the heatsink is presented, according to some embodiments. To maximize the heat dissipation for a temperature therapy device, it can be useful to form the fins 602 as thin as possible. In some embodiments, each fin 608 can include a thickness 610 in a range of approximately 0.2-0.4 mm. In an example, each fin 608 can have a thickness 610 of approximately 0.3 mm. In some embodiments, each fin 602 can have a height 608 in a range of approximately 9-11 mm. In an example, each fin 602 can have a height 608 of approximately 10 mm. In some embodiments, the distance 612 between each fin 608 can be in a range of approximately 0.80 mm-1.0 mm. In an example, the distance 612 between each fin 608 can be approximately 0.95 mm. In some embodiments, the distance 614 between a fin on one side of the heatsink to another fin on another opposite side of the heatsink can be in a range of 39-41 mm. In some embodiments, the distance 614 between the fin on one end to the last fin on the corresponding opposite end of the heatsink can be approximately 40.3 mm. In some embodiments, the heatsink 600 can include approximately 10-50 fins. In an example, the heatsink 600 can include 33 fins. In some embodiments, the heatsink can have 27 fins. In some embodiments, the base 604 of the heatsink 600 can have a thickness 616 in a range of approximately 1.5-2.5 mm. In an example, the base 604 of the heatsink 600 can have a thickness 616 of approximately 2.0 mm. In some embodiments, the base 604 can have a substantially smooth bottom surface. The heatsink 600 can also have tabs 606, 607, which are discussed in FIG. 6C below.

Referring to FIG. 6C, a bottom view of the heatsink is presented, according to some embodiments. The heatsink 600 can include a first tab 606 and a second tab 607, as shown. In embodiment, as discussed above, the tabs 606, 607 of the heatsink 600 can be configured to align and/or fit into one or more notches 514 of the spacer 500 of FIGS. 5A-5D. As shown, the tabs 606, 607 may not be aligned along a horizontal direction of the figure. In some embodiments, the first and second tabs 606, 607 can be offset from one another. In some embodiments, the first tab 606 can be offset from the second tab 607 by a distance 618 in a range of approximately 4.5-6.5 mm. In an example, the first tab 606 can be offset from the second tab 607 by a distance 618 of approximately 5.6 mm. In some embodiments, the tabs 606, 607 can extend 620 from the heatsink 600. In some embodiments, the extension 620 of the tabs 606, 607 from the heatsink 600 can be in a range of approximately 1.5-3.5 mm. In an example, the extension 620 of the tabs 606, 607 from the heatsink 600 can be approximately 2.70 mm. In some embodiments, the first and second tab 606, 607 can have a width 622 in a range of approximately 3.5-5.5 mm. In an example, the first and the second tab 606, 607 can have a width 622 of approximately 4.4 mm. In some embodiments, the heatsink 600 can have a width 624 in a range of approximately 35-45 mm. In an example, the heatsink 600 can have a width 624 of approximately 40.70 mm. In some embodiments, the heatsink 600 can have a length 626 in a range of approximately 50-60 mm. In an example, the heatsink 600 can have a length 626 of approximately 57.50 mm.

Referring to FIGS. 6A-6C, in some embodiments, the heatsink can include aluminum. In an example, the heatsink can include anodized aluminum. In some embodiments, the heatsink can include aluminum 6063.

Figure 7:
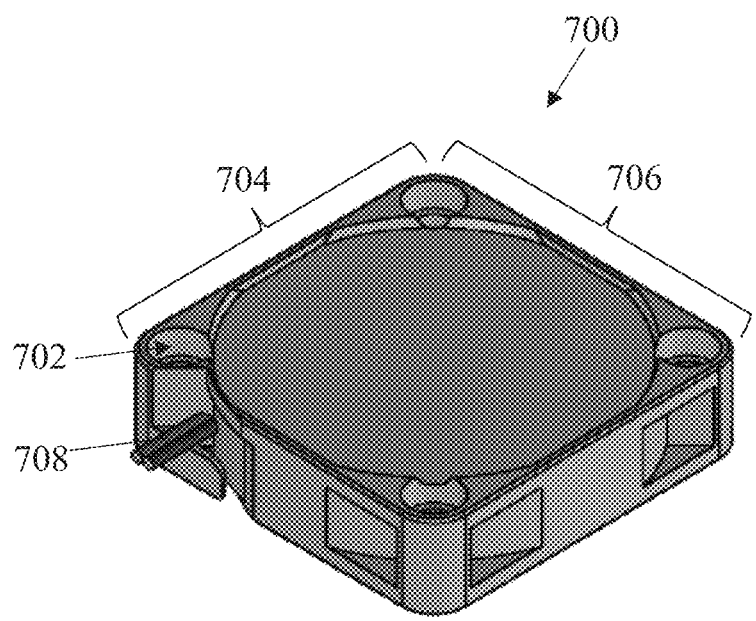
FIG. 7 illustrates a fan of the temperature modulation assembly, according to some embodiments.

Referring to FIG. 7, a fan of the temperature modulation assembly is presented, according to some embodiments. As used herein, the fan 700 shown is the same fan used in FIG. 1E. In some embodiments, the fan 700 includes a plurality of openings 702. In some embodiments, the openings 702 can be configured to receive a screw for mounting the fan to the spacer described in FIGS. 1E and 5A-5D. In some embodiments, the width 704 of the fan 700 can be in a range of approximately 35-45 mm. In an example, the width 704 of the fan 700 can be approximately 40 mm. In some embodiments, the length 706 of the fan 700 can be in a range of approximately 35-45 mm. In an example, length 706 of the fan 700 can be approximately 40 mm. The fan 700 can include wires 708 for electrical power.

Figure 8A:
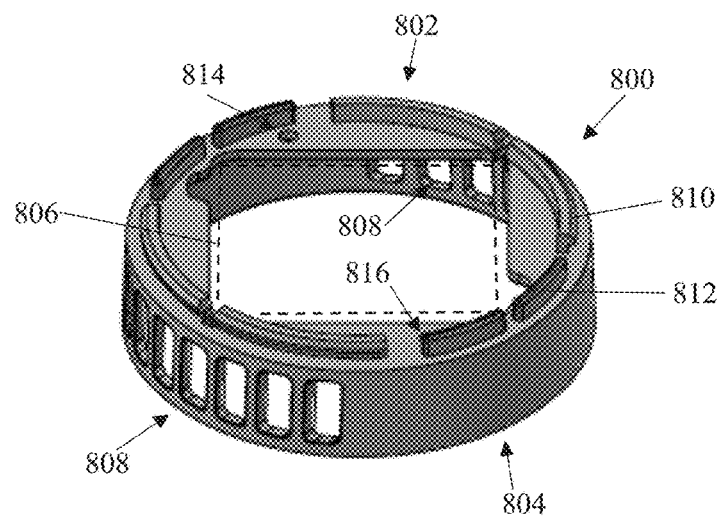
FIG. 8A illustrates a cover of the temperature modulation assembly, according to some embodiments.
Figure 8B:
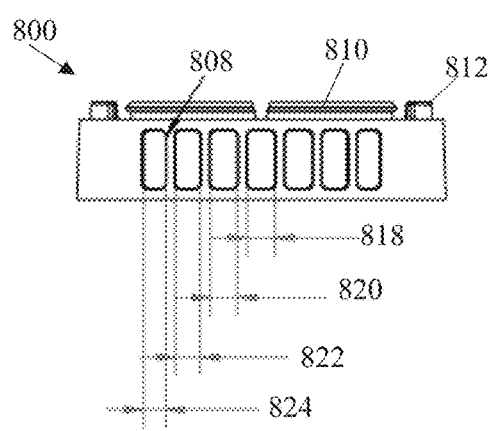
FIG. 8B illustrates a side view of the cover, according to some embodiments.
Figure 8C:
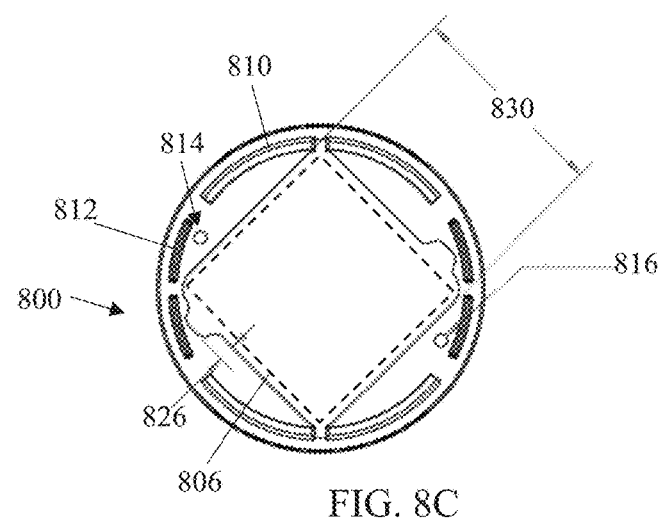
FIG. 8C illustrates a top view of the cover, according to some embodiments.
Figure 8D:
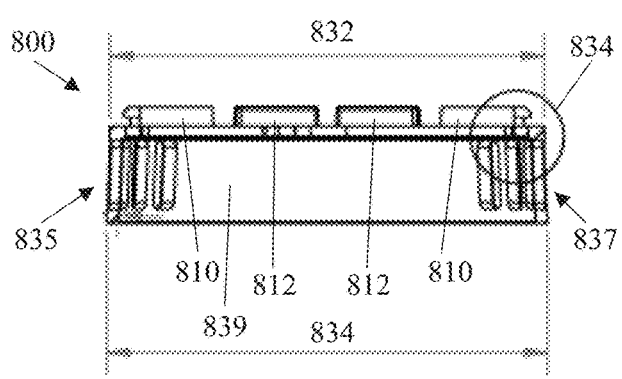
FIG. 8D illustrates another side view of the cover, according to some embodiments.
Figure 8E:
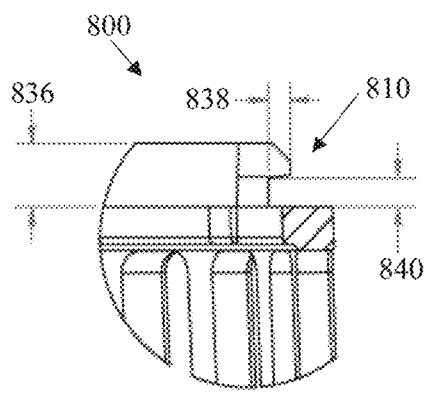
FIG. 8E illustrates a zoom-in view of a locking mechanism of the cover, according to some embodiments.

Referring to FIGS. 8A-8E, various views of a cover are presented, according to some embodiments. In some embodiments, the cover can be an intermediate structure configured to enclose and/or house the spacer from FIGS. 5A-5D, heatsink from FIGS. 6A-6C and the fan from FIG. 7, e.g., as shown together in FIG. 1E. The cover can also be configured to secure the top layer of FIGS. 10A-10D to the spacer of FIGS. 5A-5D. FIG. 8A illustrates a cover of the temperature modulation assembly. FIG. 8B illustrates a side view of the cover. FIG. 8C illustrates a top view of the cover. FIG. 8D illustrates another side view of the cover. FIG. 8E illustrates a zoom-in view of a locking mechanism of the cover.

Referring to FIG. 8A, a cover of the temperature modulation assembly is presented, according to some embodiments. In some embodiments, the cover 800 can include a top portion 802 and a bottom portion 804. In some embodiments, the cover 800 can include a central opening 806 (e.g., similar to the central opening of the spacer in FIGS. 5A-5D). In some embodiments, the central opening 806 can include a shape a similar to and/or the same shape as the fan of FIG. 7, e.g., a square opening. Although the central opening 806 can include a square opening, other shapes can be used such as a circular opening 806, polygonal opening, among other shapes. In some embodiments, as shown in FIG. 1E, the cover 800 can be positioned over a spacer, heatsink and fan during mounting and/or assembly of the temperature modulation assembly. In some embodiments, the cover 800 can include one or more vents 808. In some examples, the vent 808 functions as an exhaust vent, allowing air that has circulated near the fins of the heatsink to flow out of the temperature modulation assembly. In some examples, the vent functions as an intake vent, allowing air to flow into the temperature modulation assembly before circulating near the fins of the heatsink. In some embodiments, the vents 808 can also be referred to herein as a plurality of vents 808 or, individually, e.g., each vent 808. In some embodiments, as shown, the vents 808 can include a pseudo-square shape as shown. In some embodiments, the vents 808 can include any suitable shapes, for example, rectangular, square, circular, among other shapes.

Referring again to FIG. 8A, in some embodiments, the cover 800 can include a locking mechanism 810. In some embodiments, the locking mechanism 810 can be shaped like a wedge. In some embodiments, the locking mechanism 810 can be configured to fit into and/or lock into with a corresponding feature of a cap (e.g., cap 158 of FIG. 1E). In some embodiments, the cover 800 can include alignment features 812. In some embodiments, the alignment features 812 can be configured to secure the cap in place, e.g., the cap from FIG. 1E and FIGS. 9A-9D. In some embodiments, the alignment features 812 can include short walls that extend from the cover, e.g., without a wedge or perpendicular extended features in contrast to the locking mechanism 810. In some embodiments, the cover 800 can include a first and a second opening 814, 816. In some embodiments, the openings 814, 816 can be used for mounting the cover 800 to the spacer. In some embodiments, the first and second openings 814, 816 can be configured to receive a screw that can be used to mount into the top openings of the spacer of FIGS. 5A and 5B and/or to the openings in the fan of FIG. 7.

Referring to FIG. 8B, a side view of the cover is presented, according to some embodiments. As shown, the cover 800 can include a locking mechanism 810 and an alignment feature 812. In some embodiments, cover 800 can include one or more vents 808: a first vent 818, a second vent 820, a third vent 822 and a fourth vent 824. In some embodiments, the width of the first vent 818 can be greater than the width of the second, third and fourth vents 820, 822, 824. In some embodiments, the width of the second vent 820 can be less than the width of the first vent 818 but greater than the widths of the third and fourth vents 822, 824. In some embodiments, the third vent 824 can have a width less than the widths of the first and second vents 818, 820 and have a width greater than the width of the fourth vent 824. In some embodiments, the fourth vent 824 can have a width less than the widths of the first, second and third vents 818, 820, 822. In an example, the width of the first or most central vent 818 can be greater than the widths of the other vents 820, 822, 824, where each succeeding vent farther away from the central vent 818 can have a width that is less than the widths of the vents closer to the center. In an example, the width of the vents 818-824 can be in a range of approximately 3.00-5.00 mm.

Referring to FIG. 8C, a top view of the cover is presented, according to some embodiments. In some embodiments, the cover 800 can include a central opening 806 as discussed above. In some embodiments the first and second openings, 814, 816 from FIG. 8A are shown. As described above, the first and second openings 814, 816 can be configured to align with the top openings of the spacer of FIGS. 5A-5D. In some embodiments, the locking mechanism 810 and alignment feature 812 of FIGS. 8A and 8B are also shown. The central opening 806 can have an additional notch 826 configured to let wires from the fan pass through underneath the cover. In some embodiments, the notch 826 of the central opening can extend by approximately 2.80 mm-3.20 mm from the central opening 806. In some embodiments the central opening 806 can have a width 830 in a range of approximately 40-41 mm. In some embodiments the central opening 806 can have a width 830 of approximately 40.50 mm.

Referring to FIG. 8D, another side view of the cover is presented, according to some embodiments. As shown, the cover can be slightly tapered. In some embodiments, the cover can have a top width 832 that can be in range of approximately 62-64 mm and a bottom width 834 that can be in a range of approximately 63-65 mm. In some embodiments, the top width 832 can be approximately 63 mm and the bottom width 834 can be approximately 64 mm. In an example, the bottom width can be approximately 1 mm less than the top width. In some embodiments, the cover 800 can include one or more groups of vents 835, 837. In some embodiments, one or more groups of vents 835, 837 can be located along a wall portion 839 of the cover 800. In some embodiments, the one or more groups of vents 835, 837 can be located at separate, e.g., opposite, sides from another. In an example a first group of openings 835 can be located along one side of the wall portion 839 of the cover 800, separate and opposite from, a second group of vents 837, as shown. An exemplary locking mechanism is encircled in 834 and is further described in FIG. 8E.

Referring to FIG. 8E, a zoom-in view of a locking mechanism of the cover is presented, according to some embodiments. In some embodiments, the locking mechanism 810 can have a height 836 in a range of approximately 2.70-3.10 mm. In an example, the locking mechanism can have a height 836 of approximately 2.90 mm. In some embodiments, a wedge portion of the locking mechanism 810 can extend 838 outwardly from the cover 800 by a range of approximately 0.90 mm-1.10 mm. In an example, wedge portion of the locking mechanism 810 can extend 838 outwardly from the cover 800 by approximately 1.00 mm. In some embodiments, the wedge portion of the locking mechanism 810 can have a height 840 in a range of approximately 1.20-1.40 mm. In an example, the wedge portion of the locking mechanism 810 can have a height 840 of approximately 1.30 mm.

Referring still again to FIGS. 8A-8E, in some embodiments, the cover 800 can include a material such as a plastic and/or resin, among other materials. In a particular example, the cover 800 can include Dupont 801 resin, Dupont 2801, Acrylonitrile butadiene styrene (ABS) plastic, among other materials.

Figure 9A:
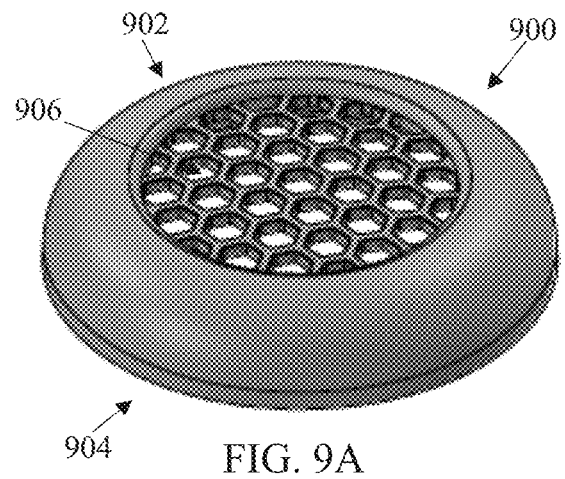
FIG. 9A illustrates a cap of the temperature modulation assembly, according to some embodiments.
Figure 9B:
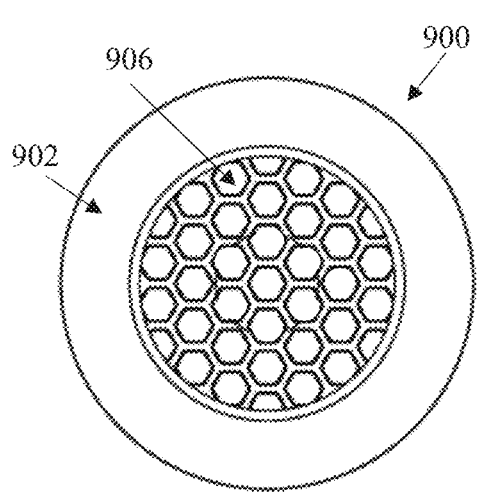
FIG. 9B illustrates a top view of the cap, according to some embodiments.
Figure 9C:
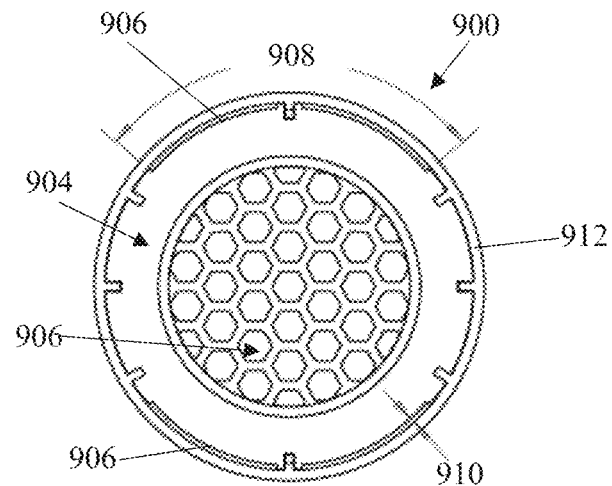
FIG. 9C illustrates a bottom view of the cap, according to some embodiments.
Figure 9D:
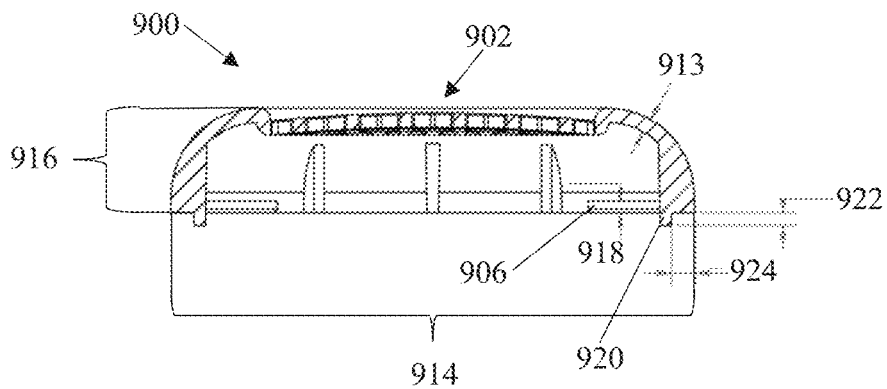
FIG. 9D illustrates a cross-sectional view of the cap, according to some embodiments.

Referring to FIGS. 9A-9D, various views of a cap are presented, according to some embodiments. In some embodiments, the cap can enclose the temperature modulation assembly and be configured to allow air to flow into the temperature modulation assembly for device cooling. In some embodiments, the cap can couple directly to the cover of FIGS. 8A-8E. FIG. 9A illustrates a cap of the temperature modulation assembly. FIG. 9B illustrates a top view of the cap. FIG. 9C illustrates a bottom view of the cap. FIG. 9D a cross-sectional view of the cap.

Referring to FIGS. 9A and 9B, multiple views of a cap are presented, according to some embodiments. In some embodiments, the cap 900 can include a top portion 902 and a bottom portion 904. In some embodiments, the cap 900 can be secured to the cover of FIGS. 8A-8E. In an example, the cap 900 can be secured by a snap fit. In some embodiments, the cap can include one or more openings 906. In some embodiments, the openings 906 of the cap 900 can be referred to as a plurality of openings 906 and/or referred to, individually, e.g., each opening 906. In some embodiments, the openings 906 of the cap 900 can be in a hexagon shape. In some embodiments, the openings 906 can be configured to provide structural support to the cap 900. In some embodiments, although the openings 906 can have a hexagon shape as shown, other shapes can be used for the openings 906. In some embodiments, the openings 906 can include a shape selected from the group consisting of a circular shape, a square shape, a polygonal shape, among other shapes. In some embodiments, the openings 906 can allow air to flow into the temperature therapy device. In an embodiment, the cap 900 may not reach or touch the top of a fan, e.g., the fan from FIG. 1E and FIG. 7.

Referring to FIG. 9C, a bottom view of a cap is presented, according to some embodiments. The bottom portion 904 of the cap 900 is shown. In some embodiments, in this view, a receiving portion 906 of the cap 900 can be seen. In some embodiments, the receiving portion 906 of the cap 900 can have a corresponding feature to receive the locking mechanism of the cover from FIGS. 8A-8E. In some embodiments, the receiving portion 906 can include a receptacle. In some embodiments, the receiving portion 906 can be a shape that is opposite to the shape of the locking mechanism from FIGS. 8A-8E, e.g., to a wedge shape. In some embodiments, the receiving portion 906 can extend 910 inward from an outer wall 912 of the cap 900. In some embodiments, the extension 910 of the receiving portion 906 can be in a range of approximately 0.70 mm-0.90 mm. In some embodiments, the extension 910 of the receiving portion 906 can be approximately 0.80 mm. In some embodiments, the receiving portion 906 can have a curved length 908 in a range of approximately 95-105 mm. In some embodiments, the cap 900 can have a curved length 908 of approximately 100 mm.

Referring to FIG. 9D, a cross-sectional view of the cap from FIGS. 9A-9C is shown, according to some embodiments. In some embodiments, the cap 900 can have a width 914 of approximately 62 mm-64 mm. In some embodiments, the cap 900 can have a width 914 of approximately 63 mm. In some embodiments, the cap 900 can have a height 916 of approximately 12 mm-13 mm. In some embodiments, the cap 900 can have a height 916 of approximately 12.5 mm. In some embodiments, the receiving portion 906 can have a height 918 in a range of approximately 1.3 mm-1.5 mm. In some embodiments, the receiving portion 906 can have a height 918 of approximately 1.5 mm. In some embodiments, the outer wall 912 can have a thickness 913 in a range of approximately 1.60 mm-1.80 mm. In some embodiments, the outer wall 912 can have a thickness 913 of approximately 1.70 mm. In some embodiments, the bottom portion 904 of the cap 900 can include an extruded portion 920. In some embodiments, the extruded portion 920 can extend 922 outward away from the cap 900 by a range of approximately 1.40 mm-1.60 mm. In some embodiments, the extruded portion 920 can extend 922 outward away from the cap 900 by approximately 1.50 mm. In some embodiments, the extruded portion 920 can be offset 924 from the outer wall 912 by a range of approximately 2.00 mm-3.00 mm.

Referring to FIGS. 9A-9D, in some embodiments, the cap 900 can include a material such as a plastic and/or resin, among other materials. In a particular example, the cap 900 can include Dupont 801 resin, Dupont 2801, Acrylonitrile butadiene styrene (ABS) plastic, among other materials.

Figure 10A:
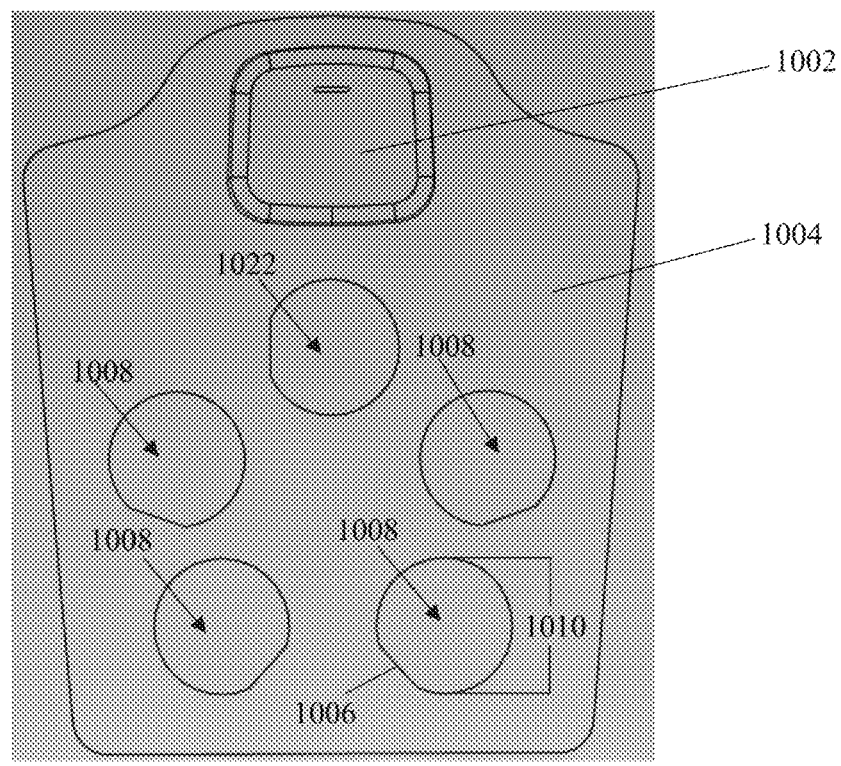
FIG. 10A illustrates a top view of a top layer of a multi-layer retention mechanism, according to some embodiments.
Figure 10B:
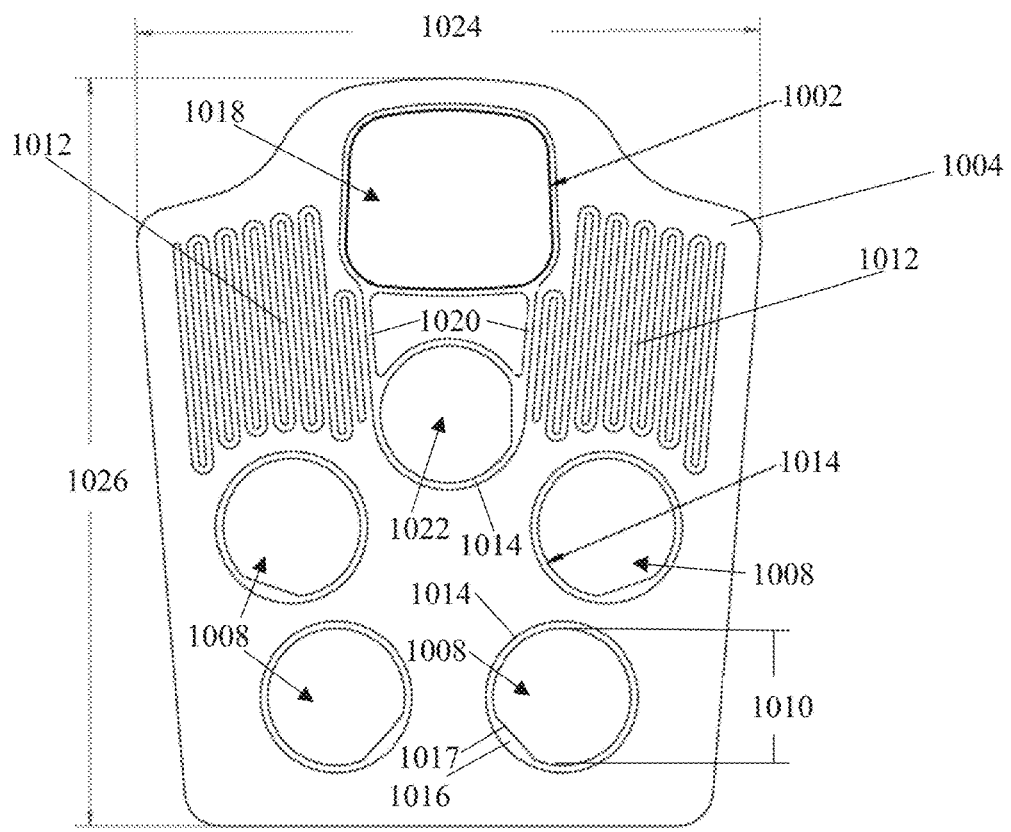
FIG. 10B illustrates a bottom view of the top layer, according to some embodiments.
Figure 10C:
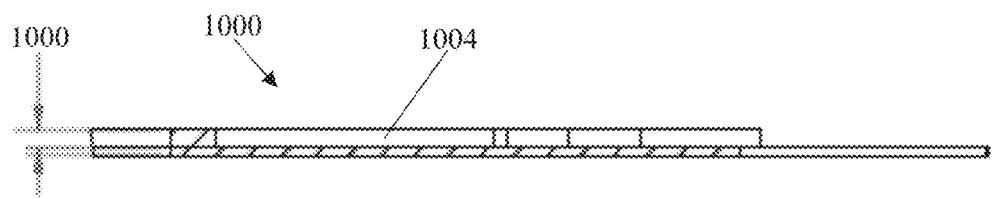
FIG. 10C illustrates a side view of the top layer, according to some embodiments.
Figure 10D:
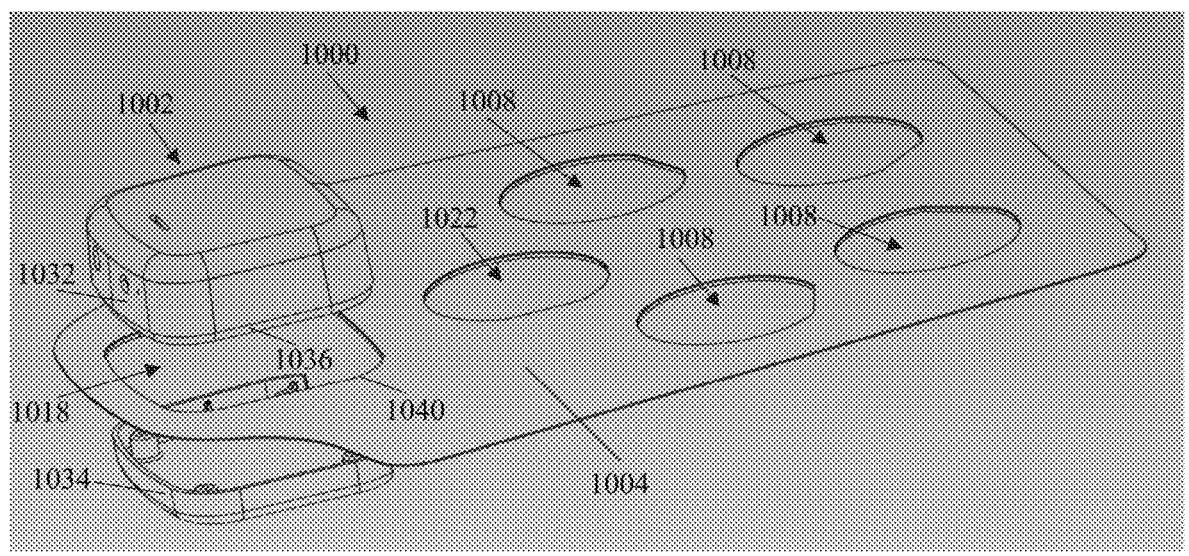
FIG. 10D illustrates a top layer with a control module of the multi-layer retention mechanism, according to some embodiments.

Referring to FIGS. 10A-10D, various views of a top layer for a multi-layer retention mechanism are shown, according to some embodiments. In some embodiments, top layer of the multi-layer retention mechanism can include a flexible fabric and/or elastic parts of the temperature therapy device. In some embodiments, the top layer can include and/or be coupled to a control module which can house control and power electronics used by the temperature therapy device. FIG. 10A shows a top view of a top layer of a multi-layer retention mechanism. FIG. 10B shows bottom view of the top layer. FIG. 10C shows a side view of the top layer. FIG. 10D shows the top layer with a control module. In some embodiments, the description of the top layer 122 of the multi-layer retention mechanism 120 described in FIGS. 1B and 1E can apply to the top layer described in FIGS. 10A-10D, and vice versa.

Referring to FIG. 10A, a top view of the top layer of the multi-layer retention mechanism is presented, according to some embodiments. As shown, the top layer 1004 of the multi-layer retention mechanism can be coupled to a control module 1002. In some embodiments, the control module 1002 can include an electronics housing and electronic parts inside the electronic housing. In some embodiments, the top layer 1004 can include a flexible fabric and/or an elastic material. In an example, the top layer 1004 can include spandex. In another example, the top layer 1004 can be entirely and/or partially made up of spandex. In some embodiments, the top layer 1004 can include alignment features 1006 which can correspond to receiving features of the spacer. In an example, the receiving features 531 and edge 515 of the spacer 500 of FIGS. 5A-5D. The top layer 1004 can include one or more openings 1008, 1022. In an example, the top layer 1004 can include one or more side openings 1008 and include a central opening 1022. In some embodiments, the openings 1008, 1022 can be circular and/or semi-circular in shape. Although the openings 1008, 1022 can include a semi-circular shape, as shown, other shapes can be used. In an example, the openings 1008, 1022 can include a shape such as square, oblong, polygonal, among other shapes. In some embodiments, the openings 1008, 1022 can include diameter 1010 in a range of approximately 57-60 mm. In an example, the diameter 1010 of the openings 1008, 1022 can be approximately 58.50 mm.

Referring to FIG. 10B, a bottom view of the top layer is presented, according to some embodiments. In some embodiments, the top layer 1004 can include rib structures 1012. In some embodiments, the rib structures 1012 can include polyurethane and/or can include a material having a hardness of approximately 80 D as measured on a durometer. In some embodiments, the rib structures 1012 can provide additional structural support to the top layer 1004. In some examples, the rib structures 1012 can obstruct the view of wires placed underneath the rib structures 1012. In some embodiments, as shown, the rib structures 1012 can be tightly packed and have an accordion shape. In some embodiments, the top layer 1004 can include a control module opening 1018 for the control module 1002. In some embodiments, the rib structures 1012 can be coupled to and/or surround edges of the control module opening 1018. In some embodiments, the rib structures 1012 can surround the top opening 1022 of the top layer 1004. Similar to the larger opening 1018, the rib structures 1012 can be coupled to and/or surround edges of the top opening 1022. In some embodiments, one or more struts 1020 can be located between the rib structures of the electronics box opening 1018 and top opening 1022. In an example, the one or more struts 1020 can provide structural support between the control module opening 1018, rib structures 1012 and the top opening 1022. In some embodiments, the rib features 1012 can be casted to the top layer 1002. In an example, the rib structures 1012 can provide structural support to the control module 1002 upon mounting the control module 1002 to couple with the top layer 1004.

Referring again to FIG. 10B, in some embodiments, the top layer 1004 can include one or more ring features 1014. In some embodiments, the ring features 1014 can be configured to lock a temperature modulation assembly in place when securing the temperature modulation assembly to the top layer 1004. In an example, the top layer 1004, and the ring features 1014 underneath, can be secured between the spacer of FIGS. 5A-5D and the cover of FIGS. 8A-8E of the temperature modulation assembly, e.g., as shown in FIGS. 1C and 1E. In some embodiments, each ring feature 1014 can include an alignment feature 1016. In some embodiments, the alignment feature 1016 can be configured to correctly orient the spacer and the cover of the temperature modulation assembly when mounting the spacer, cover, top layer and ring features together. In some embodiments, the alignment feature 1016 can include a flat edge 1017 as shown. In an example, the flat edge 1017 can be aligned with the edge 515 of the spacer of FIGS. 5A and 5B to correctly orient the spacer, cover, top layer 1004 and ring features 1014 when mounting all the components together. In some embodiments, the channels 531 shown in FIGS. 5A and 5B can be configured to conform to the alignment features 1016. In some examples, the alignment features 1016 can include extruded portions that can fit into the receiving portions 531 of FIGS. 5A and 5B. In some embodiments, the ring features 1014 can provide structural support to a temperature modulation assembly when secured to the top layer 1004. In some embodiments, similar to the rib features 1012, the ring features 1014 can also be casted to the top layer 1002. In some embodiments, the ring features 1014 can include polyurethane and/or can include a material having a hardness of approximately 80 D.

Referring still to FIG. 10B, in some embodiments, the top layer 1004 can include width 1024 in a range of approximately 260-270 mm. In an example, the width 1024 of the top layer 1004 can be approximately 265 mm. In some embodiments, the top layer 1004 can include length 1026 in a range of approximately 313-323 mm. In an example, the length 1026 of the top layer 1004 can be approximately 318 mm.

Referring to FIG. 10C, a side view of the top layer is presented, according to some embodiments. As shown, in some embodiments, the top layer 1004 can have a thickness in a range of approximately 1.00-1.50 mm. In an example, the top layer 1004 can have a thickness of approximately 1.20 mm.

FIG. 10D shows the top layer with a control module, according to some embodiments. As described in FIGS. 10A-10C and as shown, the top layer 1004 can include the openings 1008, 1018, 1022 and a control module 1002. In some embodiments, the control module 1002 can include a top housing 1032 and a bottom housing 1034. In embodiments, the top housing 1032 can include a lip portion 1036 configured to contact with and/or receive an edge 1040 of the top layer 1004 with the opening 1018 of the top layer 1004. The top housing 1032 and the bottom housing 1034 can meet and enclose around the edge 1040 of the top layer 1004, e.g., to secure the control module to the top layer 1004. The electronics components, e.g., control and/or power electronics used by the temperature therapy device, can be housed within the control module 1002, e.g., stored within the top housing 1032 and the bottom housing 1034 of the control module 1002.

Figure 11A:
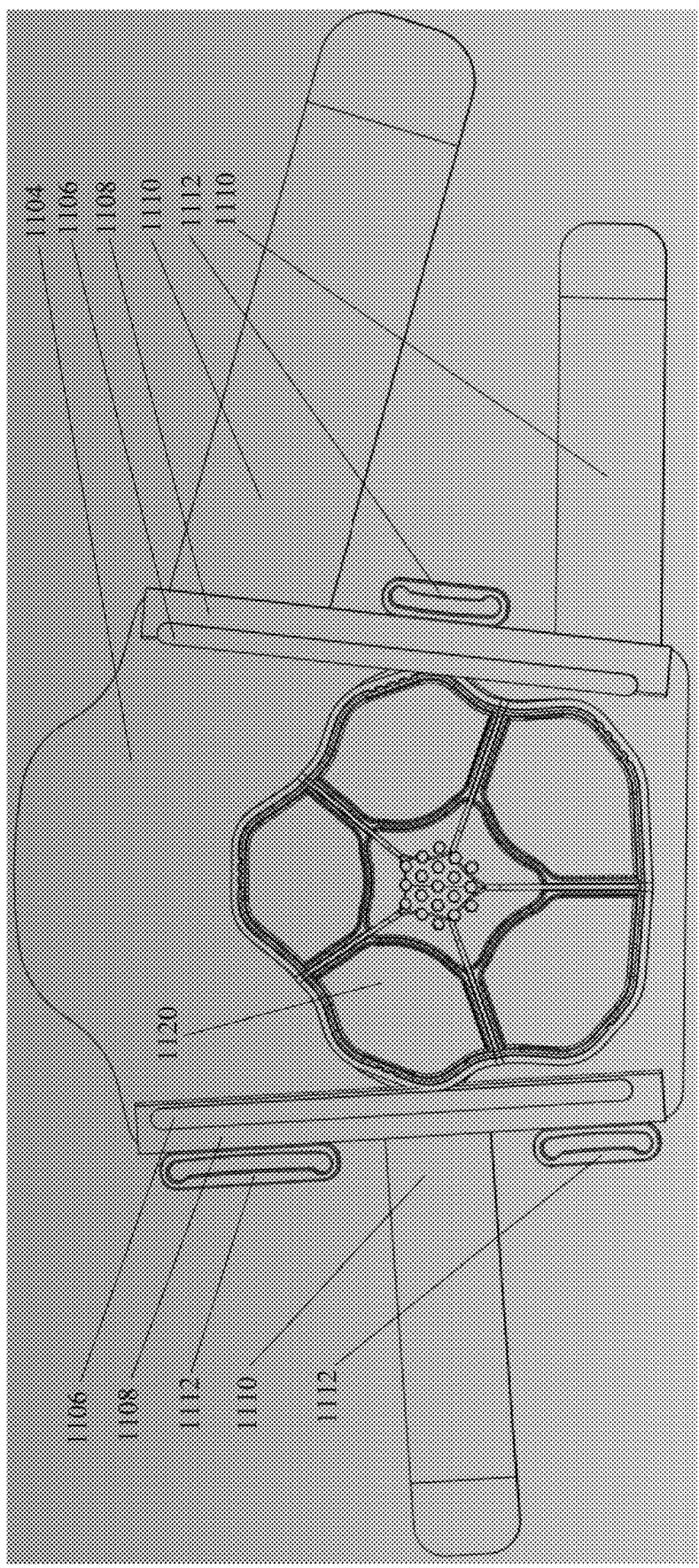
FIG. 11A illustrates a top view of a bottom layer of the multi-layer retention mechanism, according to some embodiments.
Figure 11B:
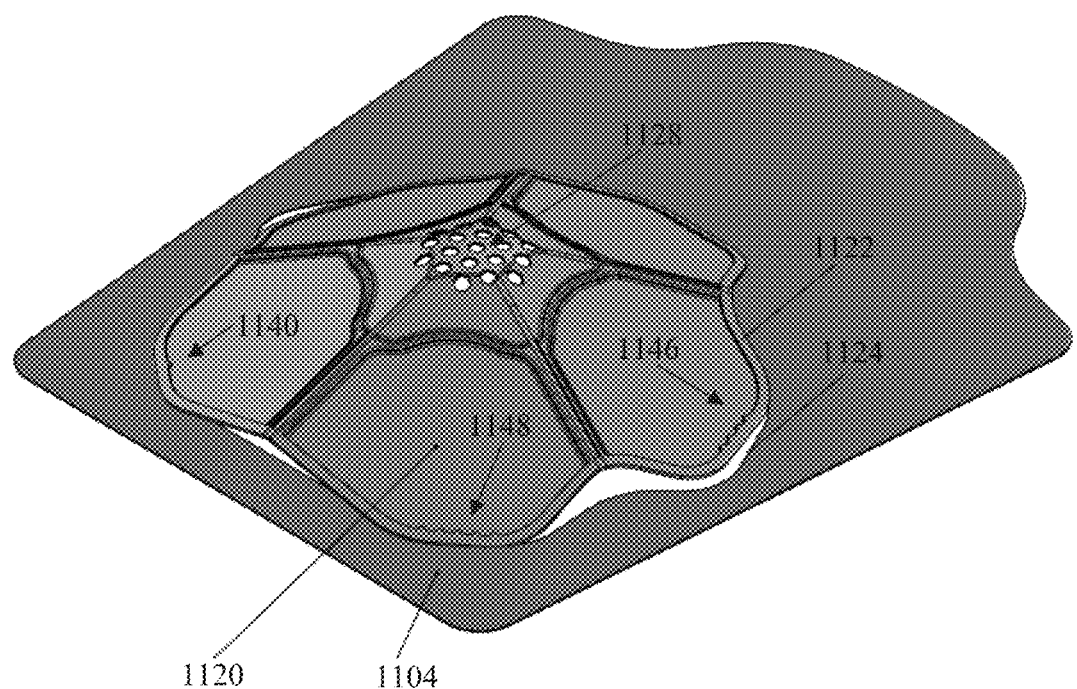
FIG. 11B illustrates the bottom layer including a silicone overmold insert, according to some embodiments.
Figure 11C:
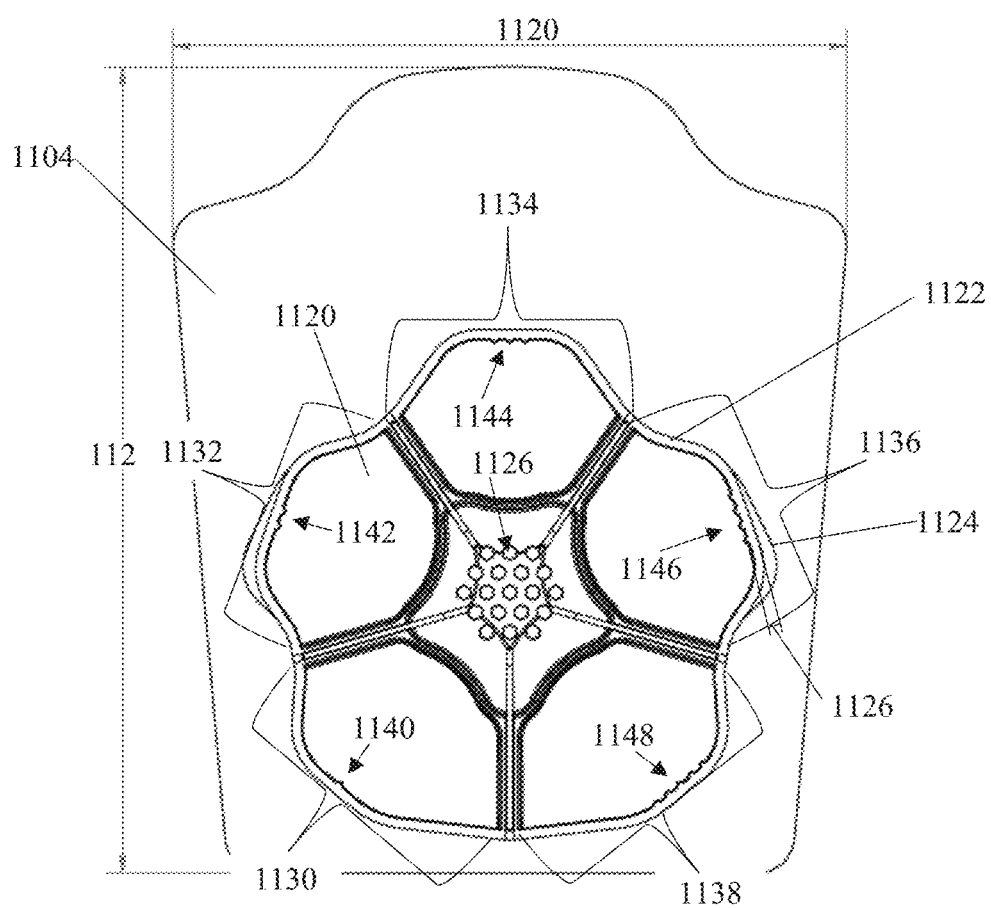
FIG. 11C illustrates a top view of the bottom layer with the silicone overmold insert, according to some embodiments.
Figure 11D:
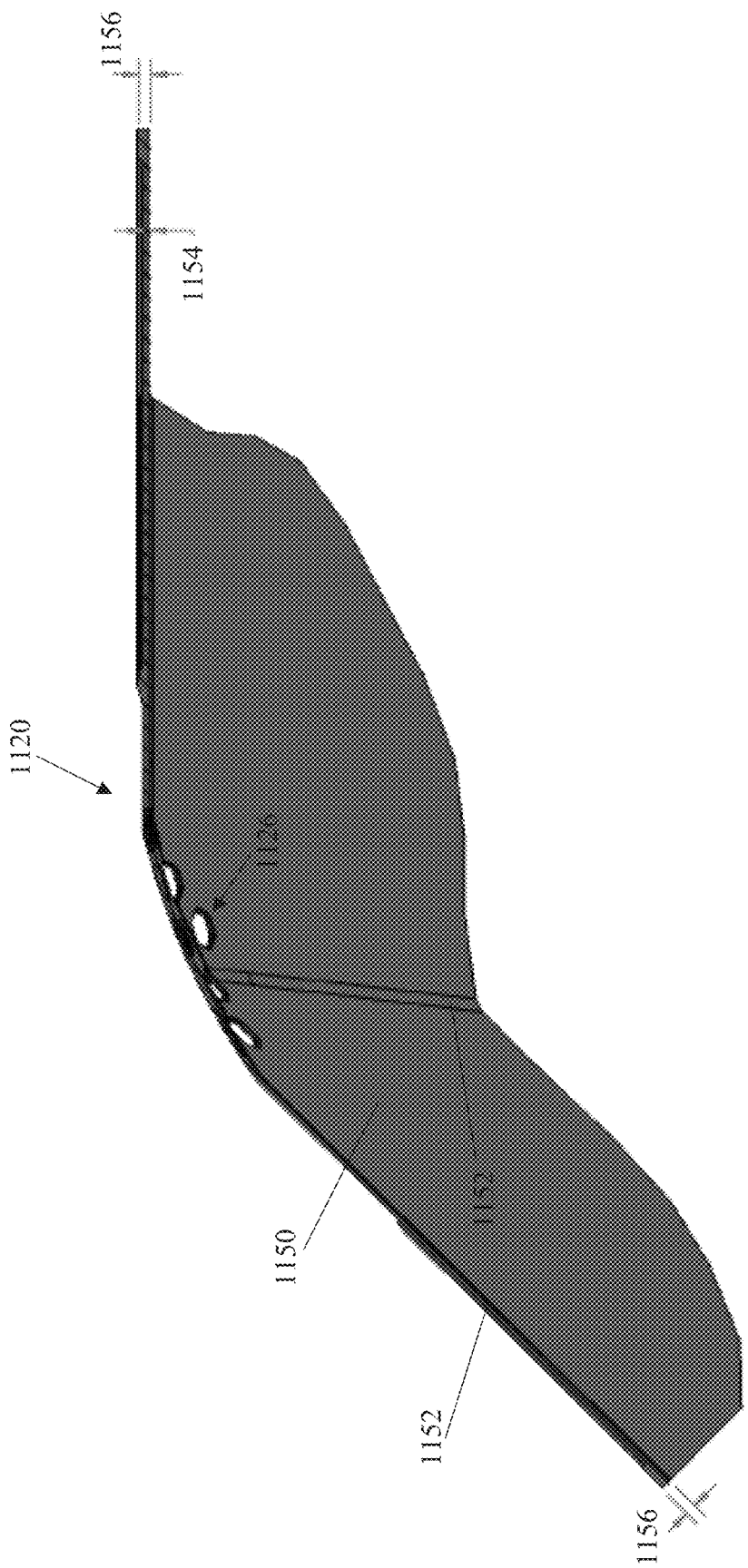
FIG. 11D illustrates a cross-sectional view of the silicone overmold insert, according to some embodiments.

Referring to FIGS. 11A-11C, various views of a bottom layer of the multi-layer retention mechanism are shown, according to some embodiments. In some embodiments, the bottom layer of the multi-layer retention mechanism can be configured to include a flexible fabric and/or various soft/elastic parts of the temperature therapy device. In an example, the bottom layer can include one or more boning mechanisms, one or more structural support pieces, one or more straps and one or more locking mechanisms. FIG. 11A illustrates a top view of a bottom layer of the multi-layer retention mechanism. FIG. 11B illustrates the bottom layer including a silicone overmold insert. FIG. 11C illustrates a top view of the bottom layer with the silicone overmold insert. FIG. 11D illustrates a cross-sectional view of the silicone overmold insert. In some embodiments, the description of the bottom layer 124 of the multi-layer retention mechanism 120 described in FIGS. 1B and 1E can apply to the bottom layer described in FIGS. 11A-11D, and vice versa.

Referring to FIG. 11A, a top view of the bottom layer of the multi-layer retention mechanism is presented, according to some embodiments. As shown, the bottom layer 1104 of the multi-layer retention mechanism can include one or more boning mechanisms 1106, one or more structural support pieces 1108, one or more straps 1110 and one or more locking mechanisms 112, e.g., similar to that described in FIGS. 1E and 1B. In some embodiments, the bottom layer 1104 and/or straps 1112 can include a flexible fabric. In an example, the bottom layer 1104 and/or straps 1112 can include spacer mesh. In a specific example, the bottom layer 1104 can include a scuba knit spacer mesh. In some embodiments, the bottom layer 1104 and/or straps 1112 can include a material selected from the group consisting of polyester and spandex. In some embodiments, the bottom layer 1104 and/or straps 1112 can include approximately 95% polyester and approximately 5% spandex. In some embodiments, the bottom layer 1104 and/or straps 1112 can include approximately 100% polyester. In some embodiments, the straps 1112 can be coupled indirectly to the boning mechanism 1106. In an example, the straps 1112 can be sewn into the bottom layer 1104 adjacent the boning mechanism 1106 to mechanically couple the straps 1112, bottom layer 1104 and boning mechanisms 1106 together. In some embodiments, the boning mechanisms 1112 can include a flat spring that is flexible in one direction but inflexible in another, e.g., perpendicular, direction. The boning mechanism 1112 can include metal and/or a metal spring. In some examples, the boning mechanism 1112 can include a steel spring. In some embodiments, the boning mechanism 1106 can be approximately 8 inches long and approximately 1.40 inches wide. In some embodiments, the boning mechanism 1106 can be located underneath the structural support pieces 1108, e.g., shown above in this figure for clarity. In some embodiments, the boning mechanisms 1112 can be sewn into a pouch and/or secured by the bottom layer 1104.

Referring to FIGS. 11B and 11C, multiple views of the bottom layer with a silicone overmold insert are presented, according to some embodiments. In some embodiments, the silicone overmold insert 1120 can be formed using a casting process. In an example, the silicone overmold insert 1120 can be cast together with the bottom layer 1104. In some embodiments, an edge 1122 of the silicone overmold insert 1120 can overlap with, and be directly coupled to, an inner edge 1124 of the bottom layer 1104. In some embodiments, the entire edge 1122 all around the silicone overmold insert 1120 can be bonded to, and/or overlap with, the inner edges 1124 of the bottom layer 1104. In an some embodiments, a liquid silicone casting process can be used to cast the silicone overmold insert 1120. In an example, a liquid silicone casting process can be used to cast the inner edge 1124 of the bottom layer 1104 to the edge 1122 of the silicone overmold insert 1120. In some embodiments, the inner edge 1124 of the bottom layer 1104 can have approximately 4 mm overlap 1126 with the edge 1122 of the silicone overmold insert 1104. In an example, the edge 1122 of the silicone overmold insert 1120 can have a thickness 1126 of approximately 4 mm. In some embodiments, the silicone overmold insert 1104 can be made up of a silicone material having a hardness of approximately 48 D as measured on a durometer (e.g., prior to casting). In some embodiments, silicone overmold insert 1120 can be referred to as a silicon substrate.

Referring again to FIGS. 11B and 11C, in some embodiments, other techniques (e.g., alternative to casting) can be used to bond the edge 1122 of the silicone overmold insert 1120 to the inner edge 1124 of the bottom layer 1104. In some embodiments, the silicone overmold insert 1120 can be sewn to the bottom layer 1104. In an example, the edge 1122 of the silicone overmold insert 1120 can be sewn to the inner edge 1124 of the bottom layer 1104. In some embodiments, the silicone overmold insert 1120 can be glued to the bottom layer 1104. In an example, the edge 1122 of the silicone overmold insert 1120 can be glued to the inner edge 1124 of the bottom layer 1104.

Referring still to FIGS. 11B and 11C, in some embodiments, the silicone overmold insert 1120 can include mechanical support features 1128. As used herein, the mechanical support features can also be referred to as patterned depressions 1128. In some embodiments, the one or more mechanical support features 1128 can be in the shape of a hexagon and/or a honeycomb configuration (e.g., as shown in FIGS. 11B-11C). In some embodiments, the mechanical support features 1128 can include a thin layer within the features 1128. In some embodiments, the thin layer within the mechanical support features 1128 can be configured to have greater elasticity in comparison to the rest of the silicone overmold insert 1120. In some embodiments, mechanical support features 1128 can be configured to allows a user's body part to bend and move while the device is positioned over the user's body part, e.g., as applied to user's knee. In an example the thin layer within the mechanical support features 1128 can be configured to stretch and allow a user's body part, e.g., knee cap, to comfortably fit on the temperature therapy device. In some embodiments, the thin layer can have a thickness in a range of 0.1-0.3 mm. In an example, the thin layer of the mechanical support feature 1128 can have a thickness of approximately 0.2 mm. In some embodiments, the mechanical support features can have a diameter within a range of approximately 20 mm-50 mm. In an example, the diameter of the mechanical support features can be approximately 38 mm.

Referring yet again to FIGS. 11B and 11C, in some embodiments, the silicone overmold insert 1120 can have one or more subdivided portions 1130-1138. Each of the subdivided portions 1130-1138 can correspond to a separate, different, temperature modulation assembly. In some embodiments, a notch and/or dot 1140-1148 can be used to assist an operator determine which temperature modulation assembly to attach to a corresponding subdivided portion 1130-1138 of the silicone overmold insert 1120 during manufacturing or fabrication. In some embodiments, the subdivided portions 1130-1138 are not identical and/or symmetrical. For example, as shown, each individual notch 1140-1148 can be different from one another. In an example, one notch 1140 can include only one feature as shown, other notches 1142, 1144, 1146 and 1148 can include one or more features as shown. In an example, the number of notches can determine which temperature modulation assembly is to be coupled to the silicone overmold insert 1120. For example, a first temperature modulation assembly can be mounted to the subdivided portion 1130 that includes the single notch 1140, a second temperature modulation assembly can be mounted to the subdivided portion 1132 that includes two notches 1142, and so on. In some embodiments, there can be one to five notches, e.g., corresponding to up to five temperature modulation assemblies. As described above, in some embodiments, a temperature therapy device can include one or more, e.g. greater than five, temperature modulation assemblies. In an example, the notches 1140-1148 can be shaped to fit into and/or align to the corresponding notches of one or more heat spreaders of the temperature modulation assembly. In one example, notch 1140 can fit into and/or align to the notch 328 of FIG. 3A.

Referring to FIG. 11D, a cross-sectional view of the silicone overmold insert is presented, according to some embodiments. The silicone overmold insert 1120 can have main body 1150 and support portions 1152. In some embodiments, the main body 1150 can have a thickness 1154 in a range of approximately 0.7-0.9 mm. In an example, the main body 1150 can have a thickness 1154 of approximately 0.8 mm. In some embodiments, the support portions 1152 can have a thickness 1156 in a range of approximately 1.50-1.70 mm. In an example, the support portions 1152 can have a thickness 1156 of approximately 1.60 mm. In some embodiments, the thickness 1156 of the support portions 1152 can be approximately twice and/or greater than twice that of the thickness of the main body 1150.

Some non-limiting examples of a temperature therapy device have been described. Additional embodiments of temperature therapy devices are described in U.S. Provisional Patent Application No. 63/090,987, which is incorporated by reference herein. Furthermore, some non-limiting examples of components of a temperature therapy device have been described. Additional embodiments of such components, including flexible thermal spreaders (e.g., heat spreader 146, 300), heating and/or cooling elements (e.g., thermoelectric coolers (TECs) 150, 400), flexible substrates (e.g., flexible layers of a multi-layer retention mechanism 102, 120), and coupling materials (e.g., adhesives, tapes, etc.) are also described in U.S. Provisional Patent Application No. 63/090,987.

Some embodiments of a temperature therapy device including a thermoelectric cooler (TEC) have been described. A TEC is one example of a temperature control (e.g., heating and/or cooling) component that may be used in the temperature therapy device. In some embodiments, heating and/or cooling components other than a TEC may be used. For example, a Peltier device, a Peltier heater, a Peltier heat pump, or any other suitable heating and/or cooling component may be used.

Computer Systems

Figure 12:
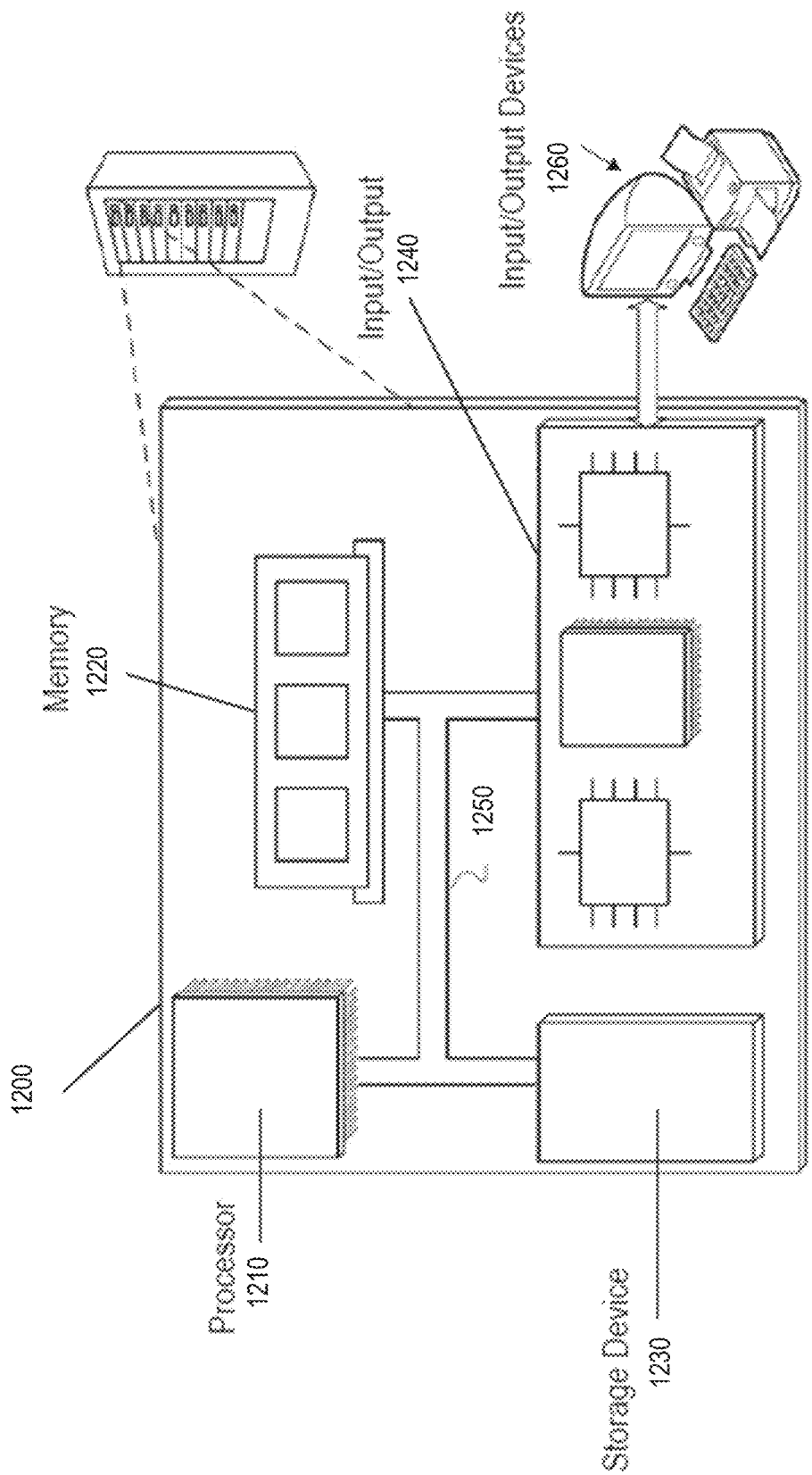
FIG. 12 is a block diagram of an example computer system, according to some embodiments.

FIG. 12 is a block diagram of an example computer system 1200 that may be used in implementing the technology described in this document. General-purpose computers, network appliances, mobile devices, or other electronic systems may also include at least portions of the system 1200. The system 1200 includes a processor 1210, a memory 1220, a storage device 1230, and an input/output device 1240. Each of the components 1210, 1220, 1230, and 1240 may be interconnected, for example, using a system bus 1250. The processor 1210 is capable of processing instructions for execution within the system 1200. In some implementations, the processor 1210 is a single-threaded processor. In some implementations, the processor 1210 is a multi-threaded processor. The processor 1210 is capable of processing instructions stored in the memory 1220 or on the storage device 1230.

The memory 1220 stores information within the system 1200. In some implementations, the memory 1220 is a non-transitory computer-readable medium. In some implementations, the memory 1220 is a volatile memory unit. In some implementations, the memory 1220 is a non-volatile memory unit.

The storage device 1230 is capable of providing mass storage for the system 1200. In some implementations, the storage device 1230 is a non-transitory computer-readable medium. In various different implementations, the storage device 1230 may include, for example, a hard disk device, an optical disk device, a solid-date drive, a flash drive, or some other large capacity storage device. For example, the storage device may store long-term data (e.g., database data, file system data, etc.). The input/output device 1240 provides input/output operations for the system 1200. In some implementations, the input/output device 1240 may include one or more of a network interface devices, e.g., an Ethernet card, a serial communication device, e.g., an RS-232 port, and/or a wireless interface device, e.g., an 802.11 card, a 3G wireless modem, or a 4G wireless modem. In some implementations, the input/output device may include driver devices configured to receive input data and send output data to other input/output devices, e.g., keyboard, printer and display devices 1260. In some examples, mobile computing devices, mobile communication devices, and other devices may be used.

In some implementations, at least a portion of the approaches described above may be realized by instructions that upon execution cause one or more processing devices to carry out the processes and functions described above. Such instructions may include, for example, interpreted instructions such as script instructions, or executable code, or other instructions stored in a non-transitory computer readable medium. The storage device 1230 may be implemented in a distributed way over a network, for example as a server farm or a set of widely distributed servers, or may be implemented in a single computing device.

Although an example processing system has been described in FIG. 12, embodiments of the subject matter, functional operations and processes described in this specification can be implemented in other types of digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible nonvolatile program carrier for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "system" may encompass all kinds of apparatus, devices, and machines for processing data, including by way of example a programmable processor, a computer, or multiple processors or computers. A processing system may include special purpose logic circuitry, e.g., an FPGA (field programmable gate array) or an ASIC (application specific integrated circuit). A processing system may include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program can include, by way of example, general or special purpose microprocessors or both, or any other kind of central processing unit. Generally, a central processing unit will receive instructions and data from a read-only memory or a random access memory or both. A computer generally includes a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other steps or stages may be provided, or steps or stages may be eliminated, from the described processes. Accordingly, other implementations are within the scope of the following claims.

Terminology

The phraseology and terminology used herein is for the purpose of description and should not be regarded as limiting.

Measurements, sizes, amounts, and the like may be presented herein in a range format. The description in range format is provided merely for convenience and brevity and should not be construed as an inflexible limitation on the scope of the invention. Accordingly, the description of a range should be considered to have specifically disclosed all the possible subranges as well as individual numerical values within that range. For example, description of a range such as 1-20 meters should be considered to have specifically disclosed subranges such as 1 meter, 2 meters, 1-2 meters, less than 2 meters, 10-11 meters, 10-12 meters, 10-13 meters, 10-14 meters, 11-12 meters, 11-13 meters, etc.

Furthermore, connections between components or systems within the figures are not intended to be limited to direct connections. Rather, data or signals between these components may be modified, re-formatted, or otherwise changed by intermediary components. Also, additional or fewer connections may be used. The terms "coupled," "connected," or "communicatively coupled" shall be understood to include direct connections, indirect connections through one or more intermediary devices, wireless connections, and so forth.

The term "approximately", the phrase "approximately equal to", and other similar phrases, as used in the specification and the claims (e.g., "X has a value of approximately Y" or "X is approximately equal to Y"), should be understood to mean that one value (X) is within a predetermined range of another value (Y). The predetermined range may be plus or minus 20%, 10%, 5%, 3%, 1%, 0.1%, or less than 0.1%, unless otherwise indicated.

The indefinite articles "a" and "an," as used in the specification and in the claims, unless clearly indicated to the contrary, should be understood to mean "at least one." The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of" "only one of" or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The use of "including," "comprising," "having," "containing," "involving," and variations thereof, is meant to encompass the items listed thereafter and additional items.

Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A temperature modulation assembly for a temperature therapy device, the temperature modulation assembly comprising:
   a heat spreader;
   a spacer comprising a central opening and a support structure, wherein the support structure directly contacts a fan;
   a mounting plate coupled to a bottom portion of the spacer, wherein the heat spreader is disposed between the mounting plate and the spacer;
   a heatsink; and
   a heating and/or cooling device disposed within the central opening of the spacer, wherein the heating and/or cooling device is located between the heatsink and the heat spreader,
   wherein the fan is coupled to a top portion of the spacer, wherein the heatsink is disposed between the top portion of the spacer and the fan.

2. The temperature modulation assembly of claim 1, wherein the mounting plate comprises aluminum or anodized aluminum.

3. The temperature modulation assembly of claim 1, wherein the spacer comprises one or more materials selected from the group consisting of Nylon 66, Dupont 801, and Dupont 2801.

4. The temperature modulation assembly of claim 1, wherein the heatsink comprises a skived heatsink.

5. The temperature modulation assembly of claim 1, wherein the heat spreader comprises graphene and/or graphite.

6. The temperature modulation assembly of claim 1, wherein the heat spreader comprises:
   a top layer comprising silicone adhesive;
   a middle layer comprising graphene and/or graphite; and
   a bottom layer comprising silicone adhesive, wherein the middle layer is disposed between the top layer and the bottom layer.

7. The temperature modulation assembly of claim 1, wherein one or more strain relief fingers are formed in the heat spreader.

8. The temperature modulation assembly of claim 7, wherein the one or more strain relief fingers extend radially from an edge of the heat spreader toward a central portion of the heat spreader.

9. The temperature modulation assembly of claim 1, further comprising a primer layer disposed between the heat spreader and the mounting plate.

10. The temperature modulation assembly of claim 1, further comprising:
    a cover disposed over the spacer and disposed circumferentially around the heatsink and fan; and
    a portion of a multi-layer retention mechanism disposed between the cover and the spacer.

11. The temperature modulation assembly of claim 10, wherein the portion of the multi-layer retention mechanism disposed between the cover and the spacer includes a portion of a top layer of the multi-layer retention mechanism and a ring feature of the multi-layer retention mechanism.

12. The temperature modulation assembly of claim 11, further comprising a cap coupled to the cover, wherein the cap comprises a plurality of openings configured to provide air flow into and/or out of the temperature modulation assembly.

13. The temperature modulation assembly of claim 1, wherein the heating and/or cooling device comprises a thermoelectric cooler (TEC).

14. The temperature modulation assembly of claim 1, wherein the support structure comprises a columnal structure.

15. The temperature modulation assembly of claim 1, wherein the support structure comprises an opening configured to receive a screw.

16. The temperature modulation assembly of claim 1, wherein a portion of the fan that this is in direct contact with the support structure extends past the heatsink.

* * * * *